US011825850B2

(12) United States Patent
Bowen et al.

(10) Patent No.: US 11,825,850 B2
(45) Date of Patent: Nov. 28, 2023

(54) INSECT INHIBITORY PROTEINS

(71) Applicant: Monsanto Technology LLC, St. Louis, MO (US)

(72) Inventors: David J. Bowen, Wildwood, MO (US); Catherine A. Chay, Ballwin, MO (US); Arlene R. Howe, Clarkson Valley, MO (US); Matthew S. Marengo, Wildwood, MO (US); Jason Meyer, O'Fallon, MO (US); Jason S Milligan, Troy, IL (US); Brian E. Weiner, Chapel Hill, NC (US)

( * ) Notice: Subject to any disclaimer, the term of this patent is extended or adjusted under 35 U.S.C. 154(b) by 0 days.

(21) Appl. No.: 17/556,428

(22) Filed: Dec. 20, 2021

(65) Prior Publication Data

US 2022/0256863 A1 Aug. 18, 2022

Related U.S. Application Data

(60) Provisional application No. 63/128,775, filed on Dec. 21, 2020.

(51) Int. Cl.

| | |
|---|---|
| ***A01N 63/50*** | (2020.01) |
| ***C07K 14/32*** | (2006.01) |
| ***C12N 15/82*** | (2006.01) |
| ***C12Q 1/68*** | (2018.01) |
| ***C07K 14/325*** | (2006.01) |
| ***C12Q 1/6895*** | (2018.01) |

(52) U.S. Cl.

CPC ............ *A01N 63/50* (2020.01); *C07K 14/325* (2013.01); *C12N 15/8286* (2013.01); *C12Q 1/6895* (2013.01)

(58) Field of Classification Search

CPC .. A01N 63/50; C07K 14/325; C12N 15/8286; C12Q 1/6895

See application file for complete search history.

(56) References Cited

U.S. PATENT DOCUMENTS

| | | | | |
|---|---|---|---|---|
| 5,188,642 | A | 2/1993 | Shah et al. | |
| 5,312,910 | A | 5/1994 | Kishore et al. | |
| 5,500,365 | A | 3/1996 | Fischhoff et al. | |
| 5,627,061 | A | 5/1997 | Barry et al. | |
| 5,633,435 | A | 5/1997 | Barry et al. | |
| 5,728,925 | A | 3/1998 | Herrera-Estrella et al. | |
| 5,750,871 | A | 5/1998 | Moloney et al. | |
| 5,880,275 | A | 3/1999 | Fischhoff et al. | |
| 6,033,874 | A | 3/2000 | Baum et al. | |
| 6,365,807 | B1 | 4/2002 | Christou et al. | |
| 6,501,009 | B1 | 12/2002 | Romano | |
| 6,551,962 | B1 | 4/2003 | Pershing et al. | |
| 6,713,063 | B1 | 3/2004 | Malvar et al. | |
| 6,962,705 | B2 | 11/2005 | Malvar et al. | |
| 7,026,528 | B2 | 4/2006 | Cheng et al. | |
| 7,064,249 | B2 | 6/2006 | Corbin et al. | |
| 7,070,982 | B2 | 7/2006 | Malvar et al. | |
| 7,193,133 | B2 | 3/2007 | Lassner et al. | |
| 7,510,878 | B2 | 3/2009 | Abad et al. | |
| 7,772,465 | B2 | 8/2010 | Abad et al. | |
| 7,812,129 | B1 | 10/2010 | Abad et al. | |
| 8,344,207 | B2 | 1/2013 | Bogdanova et al. | |
| 8,609,936 | B2 | 12/2013 | Baum et al. | |
| 10,059,959 | B2 | 8/2018 | Baum et al. | |
| 10,155,960 | B2 | 12/2018 | Bowen et al. | |
| 10,227,608 | B2 | 3/2019 | Barry et al. | |
| 10,233,217 | B2 | 3/2019 | Baum et al. | |
| 10,487,123 | B2 * | 11/2019 | Baum ................ | C12N 15/8286 |
| 10,494,408 | B2 | 12/2019 | Baum et al. | |
| 10,611,806 | B2 | 4/2020 | Baum et al. | |
| 10,626,151 | B2 | 4/2020 | Bowen et al. | |
| 10,669,317 | B2 | 6/2020 | Baum et al. | |
| 10,703,782 | B2 | 7/2020 | Baum et al. | |
| 2001/0042257 | A1 | 11/2001 | Connor-Ward et al. | |
| 2003/0110531 | A1 | 6/2003 | Dan et al. | |

(Continued)

FOREIGN PATENT DOCUMENTS

| | | |
|---|---|---|
| EP | 0218571 | 2/1993 |
| EP | 0189707 | 8/1993 |

(Continued)

OTHER PUBLICATIONS

Guo et al., 2004, Protein tolerance to random amino acid change. Proceedings of the National Academy of Sciences, 101(25), 9205-9210 (Year: 2004).*

Pillai-Kastoori et al., 2020, Antibody validation for Western blot: By the user, for the user. Journal of Biological Chemistry, 295(4), 926-939 (Year: 2020).*

Saper et al., 2005, An open letter to our readers on the use of antibodies. J. Comp. Neurol. 493, 477-478 (Year: 2005).*

Wu et al., 2007, Adaptive evolution of cry genes in Bacillus thuringiensis: implications for their specificity determination. Genomics, Proteomics & Bioinformatics, 5(2), 102-110 (Year: 2007).*

Sambrook et al. (2006). The condensed protocols: from molecular cloning: a laboratory manual (Third Edition). Cold Spring Harbor, NY: Cold spring harbor laboratory press (Year: 2006).*

(Continued)

*Primary Examiner* — Weihua Fan
*Assistant Examiner* — Santosh Sharma
(74) *Attorney, Agent, or Firm* — DENTONS US LLP; Timothy K. Ball

(57) ABSTRACT

Pesticidal proteins exhibiting toxic activity against Lepidopteran pest species are disclosed, and include, but are not limited to, TIC4029, TIC4029_1, and TIC4029_8. DNA constructs are provided which contain a recombinant nucleic acid sequence encoding one or more of the disclosed pesticidal proteins. Transgenic plants, plant cells, seed, and plant parts resistant to Lepidopteran infestation are provided which contain recombinant nucleic acid sequences encoding pesticidal proteins of the TIC4029 class. Methods for detecting the presence of the recombinant nucleic acid sequences or the proteins of the TIC4029 class in a biological sample, and methods of controlling Lepidopteran species pests using any of the TIC4029, TIC4029_1, and TIC4029_8 pesticidal proteins are also provided.

35 Claims, 2 Drawing Sheets

Specification includes a Sequence Listing.

(56) References Cited

U.S. PATENT DOCUMENTS

| | | | | |
|---|---|---|---|---|
| 2004/0197916 | A1* | 10/2004 | Carozzi | C07K 14/325 536/23.6 |
| 2006/0021087 | A1 | 1/2006 | Baum et al. | |
| 2006/0112447 | A1 | 5/2006 | Bogdanova et al. | |
| 2008/0172762 | A1 | 7/2008 | Cerf et al. | |
| 2008/0256667 | A1 | 10/2008 | Dersch et al. | |
| 2008/0280361 | A1 | 11/2008 | Calabotta et al. | |
| 2008/0282432 | A1 | 11/2008 | Duncan et al. | |
| 2009/0138985 | A1 | 5/2009 | Martinell et al. | |
| 2009/0142837 | A1 | 6/2009 | Adams et al. | |
| 2009/0313721 | A1 | 12/2009 | Abad et al. | |
| 2010/0004176 | A1 | 1/2010 | Sampson et al. | |
| 2010/0017914 | A1 | 1/2010 | Hart et al. | |
| 2010/0077507 | A1 | 3/2010 | Abad et al. | |
| 2010/0077508 | A1 | 3/2010 | Abad et al. | |
| 2010/0137216 | A1 | 6/2010 | Carozzi et al. | |
| 2010/0160231 | A1 | 6/2010 | Sampson et al. | |
| 2010/0192256 | A1 | 7/2010 | Abad et al. | |
| 2010/0197592 | A1 | 8/2010 | Heinrichs | |
| 2010/0269221 | A1 | 10/2010 | Abad et al. | |
| 2010/0317569 | A1 | 12/2010 | Lira et al. | |
| 2010/0319092 | A1 | 12/2010 | Lira et al. | |
| 2010/0319093 | A1 | 12/2010 | Lira et al. | |
| 2011/0030096 | A1 | 2/2011 | Sampson et al. | |
| 2011/0055968 | A1 | 3/2011 | Cerf et al. | |
| 2011/0112013 | A1 | 5/2011 | Abad et al. | |
| 2011/0154536 | A1 | 6/2011 | Abad et al. | |
| 2012/0047606 | A1 | 2/2012 | Abad et al. | |
| 2012/0117690 | A1 | 5/2012 | Cerf et al. | |
| 2012/0167259 | A1 | 6/2012 | Liu et al. | |
| 2012/0192310 | A1 | 7/2012 | Abad et al. | |
| 2012/0210462 | A1 | 8/2012 | Bermudez et al. | |
| 2012/0233726 | A1 | 9/2012 | Abad et al. | |
| 2012/0266335 | A1* | 10/2012 | Larrinua | A23D 9/00 530/370 |
| 2013/0055469 | A1 | 2/2013 | Sampson et al. | |
| 2013/0097735 | A1 | 4/2013 | Bowen et al. | |
| 2013/0104259 | A1 | 4/2013 | Sampson et al. | |
| 2013/0117884 | A1 | 5/2013 | Hargiss et al. | |
| 2013/0167264 | A1 | 6/2013 | Sampson et al. | |
| 2013/0219570 | A1 | 8/2013 | Lira et al. | |
| 2013/0269060 | A1 | 10/2013 | Baum et al. | |
| 2013/0303440 | A1 | 11/2013 | Sampson et al. | |
| 2013/0310543 | A1 | 11/2013 | Sampson et al. | |
| 2014/0007292 | A1 | 1/2014 | Cerf et al. | |
| 2014/0033361 | A1 | 1/2014 | Altier et al. | |
| 2014/0033363 | A1 | 1/2014 | Sampson | |
| 2014/0196175 | A1 | 7/2014 | Sampson et al. | |
| 2014/0223598 | A1 | 8/2014 | Sampson et al. | |
| 2014/0223599 | A1 | 8/2014 | Sampson et al. | |
| 2014/0245491 | A1 | 8/2014 | Sampson et al. | |
| 2014/0298538 | A1 | 10/2014 | Heinrichs et al. | |
| 2014/0366227 | A1 | 12/2014 | Gatehouse et al. | |
| 2014/0373195 | A1 | 12/2014 | Sampson et al. | |
| 2016/0366891 | A1 | 12/2016 | Diehn et al. | |
| 2017/0327547 | A1* | 11/2017 | Baum | C12N 15/8286 |
| 2018/0100000 | A1* | 4/2018 | Bowen | G01N 33/5308 |
| 2019/0055577 | A1 | 2/2019 | Bowen et al. | |
| 2020/0229445 | A1 | 7/2020 | Bowen et al. | |
| 2022/0192200 | A1* | 6/2022 | Bowen | A01P 7/04 |

FOREIGN PATENT DOCUMENTS

| | | |
|---|---|---|
| EP | 0508909 | 8/1998 |
| EP | 0924299 | 5/2004 |
| WO | 2004074462 | 9/2004 |
| WO | 2013134523 | 9/2013 |
| WO | 2014008054 | 1/2014 |
| WO | 2015195594 | 12/2015 |
| WO | 2016061391 | 4/2016 |
| WO | 2016061392 | 4/2016 |
| WO | 2019178038 | 9/2019 |

OTHER PUBLICATIONS

Gryson et al., 2002, Detection of DNA during the refining of soybean oil. Journal of the American Oil Chemists' Society, 79(2), 171-174 (Year: 2002).*

Argôlo-Filho and Loguercio, 2013, Bacillus thuringiensis is an environmental pathogen and host-specificity has developed as an adaptation to human-generated ecological niches. Insects, 5(1), 62-91 (Year: 2013).*

Definition of word "variant". Merriam Webster Dictionary. https://www.merriam-webster.com/dictionary/variant. Accessed Feb. 24, 2023. (Year: 2023).*

Sanahuja et al. , 2011, Bacillus thuringiensis: a century of research, development and commercial applications. Plant biotechnology journal, 9(3), 283-300. (Year: 2011).*

Alphey, et al. Combining Pest Control and Resistance Management: Synergy of Engineered Insects With Bt Crops, Journal of Economic Entomology, vol. 102, Issue 2, pp. 717-732, 2009.

Arencibia, et al. An efficient protocol for sugarcane (*Saccharum* spp. L.) transformation mediated by Agrobacterium tumefaciens. Transgenic Res 7, 213-222 (1998).

Della-Cioppa, et al. Translocation of the precursor of 5-enolpyruvylshikimate-3-phosphate synthase into chloroplasts of higher plants in vitro. PNAS, vol. 83, No. 18 (1986).

ISAAA, 2016. Global Status of Commercialized Biotech/ GM Crops: 2016. ISAAA Brief No. 52 ISAAA: Ithaca, NY.

Jin, et al. Engineered Female-Specific Lethality for Control of Pest Lepidoptera. ACS Synth. Biol. 2013, 2, 3, 160-166 (2013).

Klee, et al. Cloning of an *Arabidopsis thaliana* gene encoding 5-enolpyruvylshikimate-3-phosphate synthase: sequence analysis and manipulation to obtain glyphosate-tolerant plants. Mol Gen Genet 210, 437-442 (1987).

Thompson, et al. CLUSTAL W: improving the sensitivity of progressive multiple sequence alignment through sequence weighting, position-specific gap penalties and weight matrix choice. Nucleic Acids Research, vol. 22, Issue 22, pp. 4673-4680, (1994).

Zhou, et al. Combining the high-dose/refuge strategy and self-limiting transgenic insects in resistance management—A test in experimental mesocosms. Evolutionary Applications, vol. 11, Issue 5, pp. 727-738, (2018).

International Search Report and Written Opinion regarding International App. No. PCT/US21/64286, dated May 3, 2022.

* cited by examiner

```
TIC4029     MNNNIENQCVPYNCLSNPEEVLLDGERISTGNSSIDISLSLVQLLVSNFVPGGGFLVGLI
TIC4029_1   MNNNIENQCVPYNCLSNPEEVLLDGERISTGNSSIDISLSLVQLLVSNFVPGGGFLVGLI
TIC4029_8   --------------------------MISTGNSSIDISLSLVQLLVSNFVPGGGFLVGLI
                                       *********************************

TIC4029     DFVWGIVGPSQWDAFLVQIEQLIQQRIEAYARAAAISNLEGIGNNFNIYVEAFQEWEEDP
TIC4029_1   DFVWGIVGPSQWDAFLVQIEQLIQQRIEAYARAAAISNLEGIGNNFNIYVEAFQEWEEDP
TIC4029_8   DFVWGIVGPSQWDAFLVQIEQLIQQRIEAYARAAAISNLEGIGNNFNIYVEAFQEWEEDP
            ************************************************************

TIC4029     NNPATRNRVVDRFRILDGLLERDIPSFRISGFEVPLLSVYTQAANLHLAILRDSVIFGER
TIC4029_1   NNPATRNRVVDRFRILDGLLERDIPSFRISGFEVPLLSVYTQAANLHLAILRDSVIFGER
TIC4029_8   NNPATRNRVVDRFRILDGLLERDIPSFRISGFEVPLLSVYTQAANLHLAILRDSVIFGER
            ************************************************************

TIC4029     WGLTTTNVNENYNRQIRHINEYADHCANTYNRGLNNLPKSTYQDWITYNRLRRDLTLTVL
TIC4029_1   WGLTTTNVNENYNRQIRHINEYADHCANTYNRGLNNLPKSTYQDWITYNRLRRDLTLTVL
TIC4029_8   WGLTTTNVNENYNRQIRHINEYADHCANTYNRGLNNLPKSTYQDWITYNRLRRDLTLTVL
            ************************************************************

TIC4029     DIVNFFPNYDNRRYPIQTVGQLTREVYTDPLINFNPQLQSVAQLPTFNVMESSAIRNPHL
TIC4029_1   DIVNFFPNYDNRRYPIQTVGQLTREVYTDPLINFNPQLQSVAQLPTFNVMESSAIRNPHL
TIC4029_8   DIVNFFPNYDNRRYPIQTVGQLTREVYTDPLINFNPQLQSVAQLPTFNVMESSAIRNPHL
            ************************************************************

TIC4029     FDVLNNLTIFTDWFSVGRNFYWGGHRVISSRIGGGNITSPIYGREANQEPPRSFTFNGPV
TIC4029_1   FDVLNNLTIFTDWFSVGRNFYWGGHRVISSRIGGGNITSPIYGREANQEPPRSFTFNGPV
TIC4029_8   FDVLNNLTIFTDWFSVGRNFYWGGHRVISSRIGGGNITSPIYGREANQEPPRSFTFNGPV
            ************************************************************

TIC4029     FRTLSNPTLRSLQQPWPAPPFNLRGVEGVEFSTPTNSFTYRGRGTVDSLTELPPQDNSVP
TIC4029_1   FRTLSNPTLRSLQQPWPAPPFNLRGVEGVEFSTPTNSFTYRGRGTVDSLTELPPQDNSVP
TIC4029_8   FRTLSNPTLRSLQQPWPAPPFNLRGVEGVEFSTPTNSFTYRGRGTVDSLTELPPQDNSVP
            ************************************************************

TIC4029     PREGYSHRLCHATFVQRSGTPFLTTGVVFSWTHRSADQNIIYPNRITQIPLVKASDLPSG
TIC4029_1   PREGYSHRLCHATFVQRSGTPFLTTGVVFSWTHRSADQNIIYPNRITQIPLVKASDLPSG
TIC4029_8   PREGYSHRLCHATFVQRSGTPFLTTGVVFSWTHRSADQNIIYPNRITQIPLVKASDLPSG
            ************************************************************

TIC4029     TTVVRGPGFTGGDILRRTSTGGFGTIRVNVNGTLTQRYRIGFRYASTVDFDFFVVRGGTT
TIC4029_1   TTVVRGPGFTGGDILRRTSTGGFGTIRVNVNGTLTQRYRIGFRYASTVDFDFFVVRGGTT
TIC4029_8   TTVVRGPGFTGGDILRRTSTGGFGTIRVNVNGTLTQRYRIGFRYASTVDFDFFVVRGGTT
            ************************************************************

TIC4029     VNNFRFPRTMNSGEELRYGSFETRSFTTPFTFTQIQDTIRTSIQGLSGNGEVYLDRIEII
TIC4029_1   VNNFRFPRTMNSGEELRYGSFETRSFTTPFTFTQIQDTIRTSIQGLSGNGEVYLDRIEII
TIC4029_8   VNNFRFPRTMNSGEELRYGSFETRSFTTPFTFTQIQDTIRTSIQGLSGNGEVYLDRIEII
            ************************************************************

TIC4029     PVTATLKAEYDLERAQKVVGALFTSTNQLALKTNITDYHIDQVSNLVDCLSDEFCLDEKR
TIC4029_1   PVT---------------------------------------------------------
TIC4029_8   PVTATLK-----------------------------------------------------
            ***
```

FIG. 1a

```
TIC4029      ELSEKVKHAKRLSDERNLLQDPNFRGINRQPDRGWRGSTDITIQGGNDVFKENYVTLPGT
TIC4029_1    ------------------------------------------------------------
TIC4029_8    ------------------------------------------------------------

TIC4029      FDECYPTYLYQKIDESKLKSDTRYQLRGYIEDSQDLEIYLIRYNAKHETVNVPGTSFLWP
TIC4029_1    ------------------------------------------------------------
TIC4029_8    ------------------------------------------------------------

TIC4029      LSVESPIGKCGEPNRCAPHIEWNPDLECSCRDGEKCAHHSHHFSLDIDVGCTDLNEDLGV
TIC4029_1    ------------------------------------------------------------
TIC4029_8    ------------------------------------------------------------

TIC4029      WVIFKIKTQDGHARLGNLEFLEEKPLLGEALARAKRAEKKWRDKRETLQLETNIVYKEAK
TIC4029_1    ------------------------------------------------------------
TIC4029_8    ------------------------------------------------------------

TIC4029      ESVDALFVNSQYDRLQADTDIAMIHAADKRVHRIREAYLPELSVIPGVNAGIFEELEGRI
TIC4029_1    ------------------------------------------------------------
TIC4029_8    ------------------------------------------------------------

TIC4029      FTAYSLYDARNVIKNGDFNNGLSCWNVKGHVDIEEQNNHRSVLVVPEWEAEVSQEVRVCP
TIC4029_1    ------------------------------------------------------------
TIC4029_8    ------------------------------------------------------------

TIC4029      GRGYILRVTAYKEGYGEGCVTIHEIEDHTDELKFSNCVEEDAYPGNTVACDNYPANQEEG
TIC4029_1    ------------------------------------------------------------
TIC4029_8    ------------------------------------------------------------

TIC4029      CTELRHSGNRGYDETYVNSTSSSTDYTAVYKEESYTGEQRYDSCESNRGYGNYTPLPAGY
TIC4029_1    ------------------------------------------------------------
TIC4029_8    ------------------------------------------------------------

TIC4029      VTKELEYFPETDKVWIEIGETEGTFIVDSVELLLMEE
TIC4029_1    -------------------------------------
TIC4029_8    -------------------------------------
```

FIG. 1b

INSECT INHIBITORY PROTEINS

CROSS REFERENCE TO RELATED APPLICATION

This application claims the benefit of U.S. provisional application Ser. No. 63/128,775, filed Dec. 21, 2020, which is herein incorporated by reference in its entirety.

INCORPORATION OF SEQUENCE LISTING

The file named "MONS484US-sequence_listing.txt" contains a DOS operating system generated computer-readable form of the Sequence Listing and was created on Dec. 9, 2021. This file is 48,197 bytes (measured in MS-Windows®), filed contemporaneously with this application by electronic submission (using the United States Patent Office EFS-Web filing system), and incorporated by reference herein in its entirety.

FIELD OF THE INVENTION

The invention generally relates to the field of insect inhibitory proteins. A novel class of proteins are disclosed exhibiting insect inhibitory activity against agriculturally relevant pests of crop plants and seeds, particularly Lepidopteran species of insects. Plants, plant parts, and seeds, including plant and microbial cells, and vectors containing a recombinant polynucleotide construct encoding one or more of the disclosed toxin proteins are provided.

BACKGROUND OF THE INVENTION

Improving crop yield from agriculturally significant plants including, among others, corn, soybean, sugarcane, rice, wheat, vegetables, and cotton, has become increasingly important. In addition to the growing need for agricultural products to feed, clothe and provide energy for a growing human population, climate-related effects and pressure from the growing population to use land other than for agricultural practices are predicted to reduce the amount of arable land available for farming. These factors have led to grim forecasts of food security, particularly in the absence of major improvements in plant biotechnology and agronomic practices. In light of these pressures, environmentally sustainable improvements in technology, agricultural techniques, and pest management are vital tools to expand crop production on the limited amount of arable land available for farming.

Insects, particularly insects within the order Lepidoptera, are considered a major cause of damage to field crops, thereby decreasing crop yields over infested areas. Lepidopteran pest species which negatively impact agriculture include, but are not limited to, Bean shoot moth (*Crocidosema aporema*), Black armyworm (*Spodoptera cosmioides*), Black cutworm (*Agrotis ipsilon*), Corn earworm (*Helicoverpa zea*), Cotton leaf worm (*Alabama argillacea*), Diamondback moth (*Plutella xylostella*), European corn borer (*Ostrinia nubilalis*), Fall armyworm (*Spodoptera frugiperda*) including Cry1Ab, Cry1Ac, and Cry1Fa resistant Fall armyworm, Old World bollworm (OWB, *Helicoverpa armigera*), Southern armyworm (*Spodoptera eridania*), Soybean looper (*Chrysodeixis includens*), Spotted bollworm (*Earias vittella*), Southwestern corn borer (*Diatraea grandiosella*), Sugarcane borer (*Diatraea saccharalis*), Sunflower looper (*Rachiplusia nu*), Tobacco budworm (*Heliothis virescens*), Tobacco cutworm (*Spodoptera litura*, also known as cluster caterpillar), Western bean cutworm (*Striacosta albicosta*), and Velvet bean caterpillar (*Anticarsia gemmatalis*).

Historically, the intensive application of synthetic chemical insecticides was relied upon as the pest control agent in agriculture. Concerns about the indiscriminate toxic effects of such insecticides, and concerns for the environment and human health, in addition to emerging resistance issues, stimulated the research and development of biological pesticides. This research effort led to the progressive discovery and use of various entomopathogenic microbial species, including bacteria.

The biological control paradigm shifted when the potential of entomopathogenic bacteria, especially bacteria belonging to the genus *Bacillus*, was discovered and developed as a biological pest control agent. Strains of the bacterium *Bacillus thuringiensis* (Bt) have been used as a source for pesticidal proteins since the dawn of molecular biology, and it was discovered that certain Bt strains exhibit a high level of toxicity against specific insects. Bt strains are known to produce delta-endotoxins that are localized within parasporal crystalline inclusion bodies at the onset of sporulation and during the stationary growth phase (e.g., Cry proteins), and are also known to produce secreted insecticidal proteins. Upon ingestion by a susceptible insect, delta-endotoxins as well as secreted toxins may exert their effects at the surface of the midgut epithelium, disrupting the cell membrane, leading to cell disruption and death. Genes encoding insecticidal proteins have also been identified in bacterial species other than Bt, including other *Bacillus* and a diversity of additional bacterial species, such as *Pseudomonas, Serratia, Xenorhabdus*, and *Photorhabdus* species, as well as other bacilli including but not limited to *Brevibacillus laterosporus, Lysinibacillus sphaericus* ("Ls" formerly known as *Bacillus sphaericus*), *Paenibacillus popilliae* and *Paenibacillus lentimorbus*. In addition, insecticidal toxins have also been identified from a variety of non-bacterial sources including ferns and other plant related species, and arachnid venoms, and the delivery of dsRNA in the diet of some pest species has been identified as an effective pest management strategy.

Crystalline and secreted soluble insecticidal toxins that are preferred for the purposes of the present invention are highly specific for the target pest species and have gained worldwide acceptance as alternatives to chemical insecticides. For example, insecticidal toxin proteins have been employed in various agricultural applications to protect agriculturally important plants from insect infestations, decrease the need for chemical pesticide applications, and increase yields. Insecticidal toxin proteins may be used to control agriculturally-relevant pests of crop plants by mechanical methods, such as spraying to disperse microbial formulations containing various bacteria strains onto plant surfaces, or alternatively by using genetic transformation techniques to produce transgenic plants and seeds expressing insecticidal toxin protein.

The use of transgenic plants expressing insecticidal toxin proteins has been globally adopted. For example, in 2016, 23.1 million hectares were planted with transgenic crops expressing Bt toxins and 75.4 million hectares were planted with transgenic crops expressing Bt toxins stacked with herbicide tolerance traits (*ISAAA*. 2016. *Global Status of Commercialized Biotech/GM Crops:* 2016. *ISAAA Brief No.* 52. *ISAAA: Ithaca, NY*). The global use of transgenic insect-protected crops and the limited number of insecticidal toxin proteins used in these crops has created a selection pressure for existing insect alleles that impart resistance to the currently-utilized insecticidal proteins.

The development of resistance in target pests to insecticidal toxin proteins creates the continuing need for discovery and development of new insecticidal toxin proteins that are useful for managing the pest populations, including those with resistance alleles. New protein toxins with management efficacy and which exhibit control over a broader spectrum of susceptible insect species will reduce the number of surviving insects which can develop resistance alleles. In addition, the use in one plant of two or more transgenic insecticidal toxin proteins toxic to the same insect pest and displaying different modes of action, or alternatively two or more different modes of toxic action (for example, a transgene encoding a dsRNA targeting an essential gene for suppression coupled with a transgene that encodes a peptide or protein toxin, both toxic to the same insect species), reduces the probability of resistance in any single target insect species. Additionally, use of self-limiting technologies such as those provided by Oxitec Ltd, when used together with the proteins of the present invention, could improve durability of the traits imparted to transgenic crops expressing proteins of the present invention (Zhou et al. 2018. Combining the high-dose/refuge strategy and self-limiting transgenic insects in resistance management—a test in experimental mesocosms. *Evol Appl* 11(5):727-738; Alphey et al. 2009. Combining pest control and resistance management: synergy of engineered insects with Bt crops. Journal of Economic Entomology, 102: 717-732).

Thus, the inventors disclose herein a novel protein from *Bacillus thuringiensis*, and exemplary recombinant proteins, that each exhibit insecticidal activity against target Lepidopteran species, particularly against Black armyworm (*Spodoptera cosmioides*), Black cutworm (*Agrotis ipsilon*), Corn earworm (*Helicoverpa zea*), European corn borer (*Ostrinia nubilalis*), Fall armyworm (*Spodoptera frugiperda*), South American podworm (*Helicoverpa gelotopoeon*), Southern armyworm (*Spodoptera eridania*), Soybean looper (*Chrysodeixis includens*), Southwestern corn borer (*Diatraea grandiosella*), Sugarcane borer (*Diatraea saccharalis*), Sunflower looper (*Rachiplusia nu*), Tobacco budworm (*Heliothis virescens*), and Velvet bean caterpillar (*Anticarsia gemmatalis*).

SUMMARY OF THE INVENTION

Disclosed herein is a novel pesticidal protein, TIC4029, and truncation variants thereof with insect inhibitory activity, which are shown to exhibit inhibitory activity against one or more pests of crop plants. The TIC4029 protein and variant proteins in the TIC4029 protein toxin class can be used alone or in combination with other insecticidal proteins and toxic agents in formulations and in planta, thus providing alternatives to insecticidal proteins and insecticide chemistries currently in use in agricultural systems.

In one embodiment, disclosed in this application is a recombinant nucleic acid molecule comprising a heterologous promoter operably linked to a polynucleotide segment encoding a pesticidal protein or pesticidal fragment thereof, wherein the pesticidal protein comprises the amino acid sequence of SEQ ID NO:2, SEQ ID NO:4, or SEQ ID NO:10; or the pesticidal protein comprises an amino acid sequence having at least 87%, or 90%, or 95%, or 98% or 99%, or about 100% identity to the amino acid sequence as set forth in SEQ ID NO:2, SEQ ID NO:4, or SEQ ID NO:10; or the polynucleotide segment hybridizes under stringent hybridization conditions to a polynucleotide having the nucleotide sequence as set forth in SEQ ID NO:1, SEQ ID NO:3, SEQ ID NO:5, SEQ ID NO:6, SEQ ID NO:7, SEQ ID NO:8; or SEQ ID NO:9. The recombinant nucleic acid molecule can comprise a sequence that functions to express the pesticidal protein in a plant, and which when expressed in a plant cell produces a pesticidally effective amount of pesticidal protein or pesticidal fragment thereof.

In another embodiment of this application the recombinant nucleic acid molecule is present within a bacterial or plant host cell. Contemplated bacterial host cells include at least the genus of *Agrobacterium, Rhizobium, Bacillus, Brevibacillus, Escherichia, Pseudomonas, Klebsiella, Pantoea*, and *Erwinia*. In certain embodiments, the *Bacillus* is a *Bacillus cereus* or *Bacillus thuringiensis*, the *Brevibacillus* is *Brevibacillus laterosporus*, or the *Escherichia* species is *Escherichia coli*. Contemplated plant host cells include a dicotyledonous plant cell and a monocotyledonous plant cell. Contemplated plant cells further include an alfalfa, banana, barley, bean, broccoli, cabbage, *brassica*, carrot, cassava, castor, cauliflower, celery, chickpea, Chinese cabbage, citrus, coconut, coffee, corn, clover, cotton (*Gossypium* sp.), a cucurbit, cucumber, Douglas fir, eggplant, *eucalyptus*, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, *Radiata* pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell.

In another embodiment, the pesticidal protein exhibits activity against Lepidopteran insects, including at least, Bean shoot moth (*Crocidosema aporema*), Black armyworm (*Spodoptera cosmioides*), Black cutworm (*Agrotis ipsilon*), Corn earworm (*Helicoverpa zea*), European corn borer (*Ostrinia nubilalis*), Fall armyworm (*Spodoptera frugiperda*), South American podworm (*Helicoverpa gelotopoeon*), Southern armyworm (*Spodoptera eridania*), Soybean looper (*Chrysodeixis includens*), Southwestern corn borer (*Diatraea grandiosella*), Sugarcane borer (*Diatraea saccharalis*), Sunflower looper (*Rachiplusia nu*), Tobacco budworm (*Heliothis virescens*), and Velvet bean caterpillar (*Anticarsia gemmatalis*).

Also contemplated in this application are plants or plant parts comprising a recombinant nucleic acid molecule encoding a pesticidal protein or fragment thereof of the TIC4029 toxin protein class. Both dicotyledonous plants and monocotyledonous plants are contemplated. In another embodiment, the plant is further selected from the group consisting of an alfalfa, banana, barley, bean, broccoli, cabbage, *brassica*, carrot, cassava, castor, cauliflower, celery, chickpea, Chinese cabbage, citrus, coconut, coffee, corn, clover, cotton, a cucurbit, cucumber, Douglas fir, eggplant, *eucalyptus*, flax, garlic, grape, hops, leek, lettuce, Loblolly pine, millets, melons, nut, oat, olive, onion, ornamental, palm, pasture grass, pea, peanut, pepper, pigeon pea, pine, potato, poplar, pumpkin, *Radiata* pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat.

In certain embodiments, seeds comprising the recombinant nucleic acid molecules are disclosed.

In still another embodiment, an insect inhibitory composition comprising the recombinant nucleic acid molecules disclosed in this application are contemplated. The insect inhibitory composition can further comprise a nucleotide sequence encoding at least one other pesticidal agent that is different from said pesticidal protein. In certain embodiments, the at least one other pesticidal agent is selected from the group consisting of an insect inhibitory protein, an insect inhibitory dsRNA molecule, and an ancillary protein. It is also contemplated that the at least one other pesticidal agent in the insect inhibitory composition exhibits activity against one or more pest species of the orders Lepidoptera, Coleoptera, or Hemiptera. The at least one other pesticidal agent in the insect inhibitory composition is in one embodiment selected from the group consisting of a Cry1A, Cry1Ab, Cry1Ac, Cry1A.105, Cry1Ae, Cry1B, Cry1C, Cry1C variants, Cry1D, Cry1E, Cry1F, Cry1A/F chimeras, Cry1G, Cry1H, Cry1I, Cry1J, Cry1K, Cry1L, Cry2A, Cry2Ab, Cry2Ae, Cry3, Cry3A variants, Cry3B, Cry4B, Cry6, Cry7, Cry8, Cry9, Cry15, Cry34, Cry35, Cry43A, Cry43B, Cry51Aa1, ET29, ET33, ET34, ET35, ET66, ET70, TIC400, TIC407, TIC417, TIC431, TIC800, TIC807, TIC834, TIC853, TIC900, TIC901, TIC1201, TIC1415, TIC2160, TIC3131, TIC836, TIC860, TIC867, TIC869, TIC1100, VIP3A, VIP3B, VIP3Ab, AXMI-AXMI-, AXMI-88, AXMI-97, AXMI-102, AXMI-112, AXMI-117, AXMI-100, AXMI-115, AXMI-113, and AXMI-005, AXMI134, AXMI-150, AXMI-171, AXMI-184, AXMI-196, AXMI-204, AXMI-207, AXMI-209, AXMI-205, AXMI-218, AXMI-220, AXMI-221z, AXMI-222z, AXMI-223z, AXMI-224z and AXMI-225z, AXMI-238, AXMI-270, AXMI-279, AXMI-345, AXMI-335, AXMI-R1 and variants thereof, IP3 and variants thereof, DIG-3, DIG-5, DIG-10, DIG-657, DIG-11 protein, IPD102Aa and homologs thereof, IPD110Aa and homologs thereof, TIC868, Cry1Da1_7, BCW003, TIC1100, TIC867, TIC867_23, TIC6757, TIC7941, IDP072Aa, TIC5290, TIC3668, TIC3669, TIC3670, IPD103 and homologs thereof, PIP-50 and PIP-65 and homologs thereof, PIP-83 and homologs thereof, and Cry1B.34.

Commodity products comprising a detectable amount of the recombinant nucleic acid molecules and toxin proteins disclosed in this application are also contemplated. Such commodity products include commodity corn bagged by a grain handler, corn flakes, corn cakes, corn flour, corn meal, corn syrup, corn oil, corn silage, corn starch, corn cereal, and the like, and corresponding soybean, rice, wheat, sorghum, pigeon pea, peanut, fruit, melon, and vegetable commodity products including, where applicable, juices, concentrates, jams, jellies, marmalades, and other edible forms of such commodity products containing a detectable amount of such polynucleotides and or polypeptides of this application, whole or processed cotton seed, cotton oil, lint, seeds and plant parts processed for feed or food, fiber, paper, biomasses, and fuel products such as fuel derived from cotton oil or pellets derived from cotton gin waste, whole or processed soybean seed, soybean oil, soybean protein, soybean meal, soybean flour, soybean flakes, soybean bran, soybean milk, soybean cheese, soybean wine, animal feed comprising soybean, paper comprising soybean, cream comprising soybean, soybean biomass, and fuel products produced using soybean plants and soybean plant parts.

Also contemplated in this application is a method of producing seed comprising the recombinant nucleic acid molecules and protein toxins from the TIC4029 protein toxin class. The method comprises planting at least one seed comprising the recombinant nucleic acid molecules disclosed in this application; growing a plant from the seed; and harvesting seed from the plant, wherein the harvested seed comprises the referenced recombinant nucleic acid molecule.

In another illustrative embodiment, a plant resistant to Lepidopteran insect infestation is provided, wherein the cells of the plant comprise the recombinant nucleic acid molecule disclosed herein.

Also disclosed in this application are methods for controlling a Lepidopteran species pest and controlling a Lepidopteran species pest infestation of a plant, particularly a crop plant. The method comprises, in one embodiment, first contacting the pest with an insecticidally effective amount of a pesticidal protein as set forth in SEQ ID NO:2, SEQ ID NO:4, or SEQ ID NO:10; or contacting the pest with an insecticidally effective amount of one or more pesticidal proteins comprising an amino acid sequence having at least 87%, or 90%, or 95%, or 98% or 99%, or about 100% identity to the amino acid sequence as set forth in SEQ ID NO:2, SEQ ID NO:4, or SEQ ID NO:10.

Further provided herein is a method of detecting the presence of a recombinant nucleic acid molecule of the TIC4029 class wherein the method comprises contacting a sample of nucleic acids with a nucleic acid probe that hybridizes under stringent hybridization conditions with genomic DNA from a plant comprising a polynucleotide segment encoding a pesticidal protein or fragment thereof provided herein, and does not hybridize under such hybridization conditions with genomic DNA from an otherwise isogenic plant that does not comprise the segment, wherein the probe is homologous or complementary to SEQ ID NO:5, SEQ ID NO:6, SEQ ID NO:7, SEQ ID NO:8; or SEQ ID NO:9, or a sequence that encodes a pesticidal protein comprising an amino acid sequence having at least 87%, or 90%, or 95%, or 98% or 99%, or about 100% amino acid sequence identity to SEQ ID NO:2, SEQ ID NO:4, or SEQ ID NO:10; subjecting the sample and probe to stringent hybridization conditions; and detecting hybridization of the probe with DNA of the sample. In some embodiments a step of detecting the presence of a member of the TIC4029 toxin protein class may comprise an ELISA or a western blot.

Also provided herein are methods of detecting the presence of a pesticidal protein or fragment thereof from the TIC4029 class wherein the method comprises contacting a sample with an immunoreactive antibody specific for binding to a TIC4029 class toxin protein; and detecting the binding of the antibody to the TIC4029 class protein, thus confirming the presence of the protein in the sample. In some embodiments the step of detecting comprises an ELISA, or a Western blot.

Also contemplated in this application is a method for controlling a Lepidopteran pest species or pest infestation in a field of transgenic crops expressing a TIC4029 class toxin protein, wherein the method comprises growing a crop plant which expresses an insecticidally effective amount of a pesticidal protein having the amino acid sequence as set forth in SEQ ID NO:8, SEQ ID NO:10, SEQ ID NO:4, SEQ ID NO:6, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, or SEQ ID NO:32; or growing a crop plant which expresses an insecticidally effective amount of one or more pesticidal proteins comprising an amino acid sequence having at least 87%, or 90%, or 95%, or 98% or 99%, or 99.5%, or about 100% identity to the amino acid sequence as set forth in SEQ ID NO:7, SEQ ID NO:9, SEQ ID NO:3, SEQ ID NO:5, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31; and optionally releasing into the field of crops containing a gene encoding the toxin protein of the present invention, one or more transgenic Lepidopteran pest species each carrying a self-limiting gene, for the purpose of preventing or delaying the onset of resistance of the one or more Lepidopteran pest species to the toxin protein. In one embodiment, the crop plants can be monocotyledonous or dicotyledonous. In another embodiment, the monocotyledonous crop plants can be corn, wheat, sorghum, rice, rye, or millet. In yet another embodiment, the dicotyledonous crop plant can be soybean, cotton, or canola. Such combination of Lepidopteran species comprising a self-limiting gene released in a reasonably close proximity to the field of transgenic crops will prevent or delay the onset of resistance of the Lepidopteran pest species lacking (or devoid of) the self-limiting gene to the toxin protein of the present invention.

BRIEF DESCRIPTION OF THE DRAWINGS

FIG. 1 is composed of two parts, 1*a* and 1*b*, and depict amino acid sequence alignment of the insect toxin proteins TIC4029 (SEQ ID NO: 2), TIC4029_1 (SEQ ID NO: 4), and TIC4029_8 (SEQ ID NO: 10). In particular, FIGS. 1*a*-1*b* show the truncations introduced into TIC4029_1 and TIC4029-8 relative to the full-length TIC4029 toxin protein. TIC4029_1 comprises a truncation of the protoxin domain. TIC4029_8 represents the tryptic core of TIC4029 and comprises truncations of the protoxin domain and a portion of the amino terminus of the mature toxin fragment.

BRIEF DESCRIPTION OF THE SEQUENCES

SEQ ID NO:1 is a nucleic acid sequence encoding a TIC4029 pesticidal protein obtained from *Bacillus thuringiensis* strain EGBS0016.

SEQ ID NO:2 is the amino acid sequence of the TIC4029 pesticidal protein.

SEQ ID NO:3 is a nucleic acid sequence encoding a TIC4029_1 pesticidal protein. TIC4029_1 is a truncation wherein the coding sequence encoding the protoxin domain of TIC4029 has been deleted.

SEQ ID NO:4 is the amino acid sequence of the TIC4029_1 pesticidal protein.

SEQ ID NO:5 is a synthetic coding sequence used for expression in a plant cell, TIC4029PL-1 encoding TIC4029.

SEQ ID NO:6 is a synthetic coding sequence used for expression in a plant cell, TIC4029PL-2 encoding TIC4029.

SEQ ID NO:7 is a synthetic coding sequence used for expression in a plant cell, TIC4029PL-3 encoding TIC4029.

SEQ ID NO:8 is a synthetic coding sequence used for expression in a plant cell, TIC4029_1PL encoding TIC4029-1.

SEQ ID NO:9 is a synthetic coding sequence used for expression of the amino acid sequence TIC4029_8. TIC4029_8 comprises amino acids 28-607 of the native TIC4029 protein and was made by deleting the N-terminal amino acids 1-27 and the amino acids of the protoxin domain after amino acid 607 of the native protein. In addition, the arginine residue of TIC4029 at amino acid position 27 of the native protein was replaced by a methionine residue.

SEQ ID NO:10 is the amino acid sequence of the TIC4029_8 pesticidal protein.

DETAILED DESCRIPTION OF THE INVENTION

One problem in the art of agricultural pest control can be characterized as a need for new toxin proteins that are efficacious against target pests, exhibit broad spectrum toxicity against target pest species, are capable of being expressed in plants without causing undesirable agronomic issues, and provide an alternative mode of action compared to current toxins that are used commercially in plants.

Novel pesticidal proteins exemplified by TIC4029 and amino acid sequence variants are disclosed herein and address each of these problems in the art, particularly against a broad spectrum of Lepidopteran insect pests, and more particularly against Bean shoot moth (*Crocidosema aporema*), Black armyworm (*Spodoptera cosmioides*), Black cutworm (*Agrotis ipsilon*), Corn earworm (*Helicoverpa zea*), European corn borer (*Ostrinia nubilalis*), Fall armyworm (*Spodoptera frugiperda*), South American podworm (*Helicoverpa gelotopoeon*), Southern armyworm (*Spodoptera eridania*), Soybean looper (*Chrysodeixis includens*), Southwestern corn borer (*Diatraea grandiosella*), Sugarcane borer (*Diatraea saccharalis*), Sunflower looper (*Rachiplusia nu*), Tobacco budworm (*Heliothis virescens*), and Velvet bean caterpillar (*Anticarsia gemmatalis*).

Reference in this application to TIC4029, "TIC4029 protein", "TIC4029 protein toxin", "TIC4029 pesticidal protein", "TIC4029-related toxins", "TIC4029-related toxins", "TIC4029 class", "TIC4029 protein toxin class", "TIC4029 toxin protein class", and the like, refer to any novel pesticidal protein or insect inhibitory protein, that comprises, that consists of, that is substantially homologous to, that is similar to, or that is derived from any pesticidal protein or insect inhibitory protein sequence of TIC4029 (SEQ ID NO:2), and the truncation toxin proteins, TIC4029_1 (SEQ ID NO:4) and TIC4029_8 (SEQ ID NO:10) and pesticidal or insect inhibitory segments thereof, or combinations thereof, that confer activity against Lepidopteran pests, including any protein exhibiting pesticidal or insect inhibitory activity if alignment of such protein with TIC4029 results in an amino acid sequence of identity of any fraction percentage from about 86% to about 100% percent. The TIC4029 proteins include both the plastid-targeted and non-plastid targeted form of the proteins.

The term "segment" or "fragment" is used in this application to describe consecutive amino acid or nucleic acid sequences that are shorter than the complete amino acid or nucleic acid sequence describing TIC4029 or TIC4029 truncation variant proteins. A segment or fragment exhibiting insect inhibitory activity is also disclosed in this application if alignment of such segment or fragment, with the corresponding section of the TIC4029 protein set forth in SEQ ID NO:2, the TIC4029_1 protein set forth in SEQ ID NO:4, or the TIC4029_8 protein set forth in SEQ ID NO:10, results in amino acid sequence identity of any fraction percentage from about 87 to about 100 percent between the segment or fragment and the corresponding segment of amino acids within the TIC4029 or TIC4029 truncation variant proteins. A fragment as described herein may comprise at least 50, at least 100, at least 250, at least 500, at least 600, at least 800, or at least 1000 contiguous amino acids of SEQ ID NO: 2, 4, or 10. A fragment as described herein may have the pesticidal activity of any of SEQ ID NO: 2, 4, or 10.

Reference in this application to the terms "active" or "activity", "pesticidal activity" or "pesticidal" or "insecticidal activity", "insect inhibitory", "pesticidally effective", or "insecticidal" refer to efficacy of a toxic agent, such as a protein toxin, in inhibiting (inhibiting growth, feeding, fecundity, or viability), suppressing (suppressing growth, feeding, fecundity, or viability), controlling (controlling the pest infestation, controlling the pest feeding activities on a particular crop containing an effective amount of the TIC4029, or TIC4029 truncation variant proteins or killing (causing the morbidity, mortality, or reduced fecundity of) a pest. These terms are intended to include the result of providing a pesticidally effective amount of a toxic protein to a pest where the exposure of the pest to the toxic protein results in morbidity, mortality, reduced fecundity, or stunting. These terms also include repulsion of the pest from the plant, a tissue of the plant, a plant part, seed, plant cells, or from the particular geographic location where the plant may be growing, as a result of providing a pesticidally effective amount of the toxic protein in or on the plant. In general, pesticidal activity refers to the ability of a toxic protein to be effective in inhibiting the growth, development, viability, feeding behavior, mating behavior, fecundity, or any measurable decrease in the adverse effects caused by an insect feeding on this protein, protein fragment, protein segment or polynucleotide of a particular target pest, including but not limited to insects of the order Lepidoptera. The toxic protein can be produced by the plant or can be applied to the plant or to the environment within the location where the plant is located. The terms "bioactivity", "effective", "efficacious" or variations thereof are also terms interchangeably utilized in this application to describe the effects of proteins of the present invention on target insect pests.

A pesticidally effective amount of a toxic agent, when provided in the diet of a target pest, exhibits pesticidal activity when the toxic agent contacts the pest. A toxic agent can be a pesticidal protein or one or more chemical agents known in the art. Pesticidal or insecticidal chemical agents and pesticidal or insecticidal protein agents can be used alone or in combinations with each other. Chemical agents include but are not limited to dsRNA molecules targeting specific genes for suppression in a target pest, organochlorides, organophosphates, carbamates, pyrethroids, neonicotinoids, and ryanoids. Pesticidal or insecticidal protein agents include the protein toxins set forth in this application, as well as other proteinaceous toxic agents including those that target Lepidopterans, as well as protein toxins that are used to control other plant pests such as Cry, Vip, and Cyt proteins available in the art for use in controlling Coleopteran, Hemipteran and Homopteran species.

It is intended that reference to a pest, particularly a pest of a crop plant, means insect pests of crop plants, particularly those Lepidoptera insect pests that are controlled by the TIC4029 protein toxin class. However, reference to a pest can also include Coleopteran, Hemipteran and Homopteran insect pests of plants, as well as nematodes and fungi when toxic agents targeting these pests are co-localized or present together with the TIC4029 protein or the TIC4029 truncation variant proteins or a protein that is 87 to about 100 percent identical to TIC4029 protein or the TIC4029 truncation variant proteins. The phrase "present together" or "co-localized" are intended to include any instance of which a target insect pest has been contacted by the TIC4029 protein toxin class as well as any other toxic agent also present in a pesticidally effective amount relative to the target insect pest. "Contacted" is intended to refer to being present in the diet of the target pest, and the diet is consumed by the target pest.

The TIC4029 or the TIC4029 truncation variant proteins are related by a common function and exhibit insecticidal activity towards insect pests from the Lepidoptera insect species, including adults, pupae, larvae, and neonates.

The insects of the order Lepidoptera include, but are not limited to, armyworms, cutworms, loopers, and heliothines in the Family Noctuidae, e.g., Fall armyworm (*Spodoptera frugiperda*), Bean shoot moth (*Crocidosema aporema*), Beet armyworm (*Spodoptera exigua*), Black armyworm (*Spodoptera cosmioides*), Southern armyworm (*Spodoptera eridania*), bertha armyworm (*Mamestra configurata*), black cutworm (*Agrotis ipsilon*), cabbage looper (*Trichoplusia ni*), soybean looper (*Pseudoplusia includens*), Sunflower looper (*Rachiplusia nu*), velvetbean caterpillar (*Anticarsia gemmatalis*), green cloverworm (*Hypena scabra*), tobacco budworm (*Heliothis virescens*), granulate cutworm (*Agrotis subterranea*), armyworm (*Pseudaletia unipuncta*), Sugarcane borer (*Diatraea saccharalis*), Sunflower looper (*Rachiplusia nu*), South American podworm (*Helicoverpa gelotopoeon*) western cutworm (*Agrotis orthogonia*); borers, casebearers, webworms, coneworms, cabbageworms and skeletonizers from the Family Pyralidae, e.g., European corn borer (*Ostrinia nubilalis*), navel orange worm (*Amyelois transitella*), corn root webworm (*Crambus caliginosellus*), sod webworm (*Herpetogramma licarsisalis*), sunflower moth (*Homoeosoma electellum*), lesser cornstalk borer (*Elasmopalpus lignosellus*); leafrollers, budworms, seed worms, and fruit worms in the Family Tortricidae, e.g., codling moth (*Cydia pomonella*), grape berry moth (*Endopiza viteana*), oriental fruit moth (*Grapholita molesta*), sunflower bud moth (*Suleima helianthana*); and many other economically important Lepidoptera, e.g., diamondback moth (*Plutella xylostella*), pink bollworm (*Pectinophora gossypiella*), and gypsy moth (*Lymantria dispar*). Other insect pests of order Lepidoptera include, e.g., cotton leaf worm (*Alabama argillacea*), fruit tree leaf roller (*Archips argyrospila*), European leafroller (*Archips rosana*) and other *Archips* species, (*Chilo suppressalis*, Asiatic rice borer, or rice stem borer), rice leaf roller (*Cnaphalocrocis medinalis*), corn root webworm (*Crambus caliginosellus*), bluegrass webworm (*Crambus teterrellus*), southwestern corn borer (*Diatraea grandiosella*), sugarcane borer (*Diatraea saccharalis*), spiny bollworm (*Earias insulana*), spotted bollworm (*Earias vittella*), American bollworm (*Helicoverpa armigera*), corn earworm (*Helicoverpa zea*, also known as soybean podworm and cotton bollworm), tobacco budworm (*Heliothis virescens*), sod webworm (*Herpetogramma licarsisalis*), Western bean cutworm (*Striacosta albicosta*), European grape vine moth (*Lobesia botrana*), citrus leafminer (*Phyllocnistis citrella*), large white butterfly (*Pieris brassicae*), small white butterfly (*Pieris rapae*, also known as imported cabbageworm), beet armyworm (*Spodoptera exigua*), tobacco cutworm (*Spodoptera litura*, also known as cluster caterpillar), and tomato leaf miner (*Tuta absoluta*).

Reference in this application to an "isolated DNA molecule", or an equivalent term or phrase, is intended to mean that the DNA molecule is one that is present alone or in combination with other compositions, but not within its natural environment. For example, nucleic acid elements such as a coding sequence, intron sequence, untranslated leader sequence, promoter sequence, transcriptional termination sequence, and the like, that are naturally found within the DNA of the genome of an organism are not considered to be "isolated" so long as the element is within the genome of the organism and at the location within the genome in which it is naturally found. However, each of these elements, and subparts of these elements, would be "isolated" within the scope of this disclosure so long as the element is not within the genome of the organism and at the location within the genome in which it is naturally found. Similarly, a nucleotide sequence encoding an insecticidal protein or any naturally occurring insecticidal variant of that protein would be an isolated nucleotide sequence so long as the nucleotide sequence was not within the DNA of the bacterium from which the sequence encoding the protein is naturally found.

A synthetic nucleotide sequence encoding the amino acid sequence of the naturally occurring insecticidal protein would be considered to be isolated for the purposes of this disclosure. For the purposes of this disclosure, any transgenic nucleotide sequence, i.e., the nucleotide sequence of the DNA inserted into the genome of the cells of a plant or bacterium, or present in an extrachromosomal vector, would be considered to be an isolated nucleotide sequence whether it is present within the plasmid or similar structure used to transform the cells, within the genome of the plant or bacterium, or present in detectable amounts in tissues, progeny, biological samples or commodity products derived from the plant or bacterium.

Reference in this application to the term "self-limiting gene" refers to one or more genes that limits survival of the host, resulting in a reduction in the host population. Such technology is offered by Oxitech Ltd. Transgenic male insects carrying a transgenic self-limiting gene are released and reproduce with wild females. As a result, the progeny inherit a copy of the self-limiting gene. The self-limiting gene disrupts the proper functioning of the insects' cells by over-producing a protein in them, interfering with the cells' ability to produce other essential proteins needed for development. By disrupting the insect's normal development, the gene prevents it from surviving to adulthood. For example, the self-limiting Diamondback Moth (*Plutella xylostella*) strain OX4319L was developed by Oxitech Ltd and carries a male-selecting gene that utilizes sequences from the sex determination gene doublesex (dsx). The gene expresses sex-alternate splicing, to engineer female-specific expression of the self-limiting gene which prevents survival of female offspring beyond the larval stage and allows for production of male only cohorts of self-limiting moths. After being released, males mate with pest females, leading to a reduction in the number of female offspring in the next generation, thereby locally suppressing *P. xylostella* populations. To facilitate the rearing of large numbers of males for release within diamondback moth production facilities, the expression of female-specific dsx within the OX4319L strain is repressed by the addition of tetracycline, or suitable analogs, into the larval feed. OX4319L also expresses the fluorescent protein, DsRed, to permit the effective monitoring of the presence of this strain in the field (Jin et al., 2013. Engineered female-specific lethality for control of pest Lepidoptera. ACS Synthetic Biology, 2: 160-166). This technology, when applied in the field with plants containing the toxin genes of the present invention, can delay or prevent the onset of resistance of pest species targeted for control by the toxin genes and proteins of the present invention, thus giving a greater durability of any plant product containing the toxin genes and proteins of the present invention. This technology could be applied to fall armyworm, corn earworm, corn rootworm, and soybean looper, as well as a host of other crop pest species.

As described further in this application, an open reading frame (ORF) encoding TIC4029 (SEQ ID NO:1) was discovered in DNA obtained from *Bacillus thuringiensis* strain EGBS0016. The coding sequence was cloned and expressed in microbial host cells to produce recombinant proteins used in bioassays. Bioassay using microbial host cell-derived proteins of TIC4029 demonstrated activity against the Lepidopteran species Black armyworm (BAW, *Spodoptera cosmioides*), Black cutworm (BCW, *Agrotis ipsilon*), Corn earworm (CEW, *Helicoverpa zea*), European corn borer (ECB, *Ostrinia nubilalis*), Fall armyworm (FAW, *Spodoptera frugiperda*), Southern armyworm (SAW, *Spodoptera eridania*), Soybean looper (SBL, *Chrysodeixis includens*), Southwestern corn borer (SWC, *Diatraea grandiosella*), Sugarcane borer (SCB, *Diatraea saccharalis*), Sunflower looper (SFL, *Rachiplusia nu*), Tobacco budworm (TBW, *Heliothis virescens*), and Velvet bean caterpillar (VBC, *Anticarsia gemmatalis*).

TIC4029_1 and TIC4029_8 disclosed herein are two different amino acid sequence deletion variants of TIC4029. TIC4029_1 comprises a deletion of the carboxy-terminal protoxin domain, i.e., amino acids beyond position 603 of the native toxin. TIC4029_1 was expressed in bacteria and assayed against BAW, SAW, and VBC and demonstrated activity against all three Lepidopteran insect pests. TIC4029_8 comprises amino acids 28-607 of the native TIC4029 protein and was made by deleting the N-terminal amino acids 1-27 and the amino acids of the protoxin domain after amino acid 607 of the native protein. In addition, the arginine residue of TIC4029 at amino acid position 27 of the native protein was replaced by a methionine residue. The TIC4029_8 toxin protein represents the tryptic core of the native TIC4029 toxin protein.

FIG. 1 presents an alignment of TIC4029, TIC4029-1, and TIC4029_8 illustrating the truncations of TIC4029_1 and TIC4029_8 relative to TIC4029. Synthetic coding sequences designed for expression of TIC4029 protein class toxins in a plant cell were produced including TIC4029 (SEQ ID NO's:5-7), TIC4029_1 (SEQ ID NO:8), and TIC4029_8 (SEQ ID NO:9).

Soybean plants expressing the toxins, TIC4029 (encoded by SEQ ID NO:5), TIC4029_1 (encoded by SEQ ID NO:8), and TIC4029_8 (encoded by SEQ ID NO:9) were assayed using leaf discs and demonstrated efficacy against SBL and suppression of SAW. Corn plants expressing TIC4029 (encoded by SEQ ID NO:7) and TIC4029_8 (encoded by SEQ ID NO:9) demonstrated efficacy against SWC, and corn plants expressing TIC4029_1 (encoded by SEQ ID NO:8) demonstrated suppression of SWC. In screenhouse trials in the United States, soybean plants expressing TIC4029 (encoded by SEQ ID NO:5) demonstrated efficacy against SBL and VBC, and suppression of SAW. Soybean plants expressing TIC4029 (encoded by SEQ ID NO:5) demonstrated efficacy against SBL, SFL, and VBC when tested in screenhouse trials in Brazil.

For expression in plant cells, the TIC4029 (SEQ ID NO:2), TIC4029_1 (SEQ ID NO:4), and TIC4029_8 (SEQ ID NO:10) proteins can be expressed to reside in the cytosol or targeted to various organelles of the plant cell. For example, targeting a protein to the chloroplast may result in increased levels of expressed protein in a transgenic plant while preventing off-phenotypes from occurring. Targeting may also result in an increase in pest resistance efficacy in the transgenic event. A target peptide or transit peptide is a short (3-70 amino acids long) peptide chain that directs the transport of a protein to a specific region in the cell, including the nucleus, mitochondria, endoplasmic reticulum (ER), chloroplast, apoplast, peroxisome and plasma membrane. Some target peptides are cleaved from the protein by signal peptidases after the proteins are transported. For targeting to the chloroplast, proteins contain transit peptides which are around 40-50 amino acids. For descriptions of the use of chloroplast transit peptides, see U.S. Pat. Nos. 5,188,642 and 5,728,925. Many chloroplast-localized proteins are expressed from nuclear genes as precursors and are targeted to the chloroplast by a chloroplast transit peptide (CTP). Examples of such isolated CTP's include, but are not limited to, those associated with the small subunit (SSU) of ribulose-1,5,-bisphosphate carboxylase, ferredoxin, ferredoxin oxidoreductase, the light-harvesting complex protein I and protein II, thioredoxin F, enolpyruvyl shikimate phosphate synthase (EPSPS), and transit peptides described in U.S. Pat. No. 7,193,133. It has been demonstrated in vivo and in vitro that non-chloroplast proteins may be targeted to the chloroplast by use of protein fusions with a heterologous CTP and that the CTP is sufficient to target a protein to the chloroplast. Incorporation of a suitable chloroplast transit peptide such as the *Arabidopsis thaliana* EPSPS CTP (CTP2) (see, Klee et al., *Mol. Gen. Genet.* 210:437-442, 1987) or the *Petunia hybrida* EPSPS CTP (CTP4) (see, della-Cioppa et al., *Proc. Natl. Acad. Sci. USA* 83:6873-6877, 1986) has been shown to target heterologous EPSPS protein sequences to chloroplasts in transgenic plants (see, U.S. Pat. Nos. 5,627,061; 5,633,435; and 5,312,910; and EP 0218571; EP 189707; EP 508909; and EP 924299). For targeting the TIC4029 or the truncation variant TIC4029 toxin protein to the chloroplast, a sequence encoding a chloroplast transit peptide is placed 5' in operable linkage and in frame to a synthetic coding sequence encoding the TIC4029 or the truncation variant TIC4029 toxin protein that has been designed for expression in plant cells.

It is contemplated that additional toxin protein sequences related to TIC4029 can be created using the amino acid sequence of TIC4029 to create novel proteins with novel properties. The TIC4029 toxin proteins can be aligned to combine differences at the amino acid sequence level into novel amino acid sequence variants and making appropriate changes to the recombinant nucleic acid sequence encoding variants.

It is contemplated that improved variants of the TIC4029 protein toxin class can be engineered in planta by using various gene editing methods known in the art. Such technologies used for genome editing include, but are not limited to, ZFN (zinc-finger nuclease), meganucleases, TALEN (Transcription activator-like effector nucleases), and CRISPR (Clustered Regularly Interspaced Short Palindromic Repeats)/Cas (CRISPR-associated) systems. These genome editing methods can be used to alter the toxin protein coding sequence transformed within a plant cell to a different toxin coding sequence. Specifically, through these methods, one or more codons within the toxin coding sequence is altered to engineer a new protein amino acid sequence. Alternatively, a fragment within the coding sequence is replaced or deleted, or additional DNA fragments are inserted into the coding sequence, to engineer a new toxin coding sequence. The new coding sequence can encode a toxin protein with new properties such as increased activity or spectrum against insect pests, as well as provide activity against an insect pest species wherein resistance has developed against the original insect toxin protein. The plant cell comprising the gene edited toxin coding sequence can be used by methods known in the art to generate whole plants expressing the new toxin protein.

It is also contemplated that fragments of TIC4029 or protein variants thereof can be truncated forms wherein one or more amino acids are deleted from the N-terminal end, C-terminal end, the middle of the protein, or combinations thereof wherein the fragments and variants retain insect inhibitory activity. These fragments can be naturally occurring or synthetic variants of TIC4029 or derived protein variants but should retain the insect inhibitory activity of at least TIC4029. Examples of truncated variant proteins of TIC4029 include TIC4029_1 (SEQ ID NO:4) and TIC4029_8 (SEQ ID NO:10).

Proteins that resemble the TIC4029 proteins can be identified and compared to each other using various computer-based algorithms known in the art (see Table 1). Amino acid sequence identities reported in this application are a result of a Clustal W alignment using these default parameters: Weight matrix: blosum, Gap opening penalty: 10.0, Gap extension penalty: 0.05, Hydrophilic gaps: On, Hydrophilic residues: GPSNDQERK, Residue-specific gap penalties: On (Thompson, et al (1994) Nucleic Acids Research, 22:4673-4680). Percent amino acid identity is further calculated by the product of 100% multiplied by (amino acid identities/length of subject protein). Other alignment algorithms are also available in the art and provide results similar to those obtained using a Clustal W alignment and are contemplated herein.

It is intended that a protein exhibiting insect inhibitory activity against a Lepidopteran insect species is related to TIC4029 if the protein is used in a query, e.g., in a Clustal W alignment, and the proteins of the present invention as set forth as SEQ ID NO:2 are identified as hits in such alignment in which the query protein exhibits at least 87% to about 100% amino acid identity along the length of the query protein that is about 87%, 88%, 89%, 90%, 91%, 92%, 93%, 94%, 95%, 96%, 97%, 98%, 99%, 100%, or any fraction percentage in this range.

In addition to percent identity, TIC4029 and the truncation variants of TIC4029 can also be related by primary structure (conserved amino acid motifs), by length and by other characteristics. Characteristics of the TIC4029 protein toxins class are reported in Table 1.

TABLE 1

Selected characteristics of TIC4029 and truncation variant protein toxins.

| Protein | Molecular Weight (in Daltons) | Amino Acid Length | Isoelectric Point | Charge at PH 7.0 | No. of Hydro-phobic Amino Acids | No. of Polar Amino Acids | No. of Stongly Basic (−) Amino Acids | No. of Strongly Acidic Amino Acids |
|---|---|---|---|---|---|---|---|---|
| TIC4029 | 133674.75 | 1177 | 4.8540 | −32.0 | 593 | 584 | 139 | 159 |
| TIC4029_1 | 68156.27 | 603 | 6.7263 | 1.0 | 317 | 286 | 60 | 55 |
| TIC4029_8 | 65610.58 | 581 | 8.5413 | 6.0 | 307 | 274 | 60 | 50 |

As described further in the Examples of this application, synthetic nucleic acid molecule sequences encoding TIC4029, TIC4029_1, and TIC4029_8 were designed for use in plants, encoded respectively by SEQ ID NOs:5-7 (TIC4029), SEQ ID NO:8 (TIC4029_1), and SEQ ID NO:9 (TIC4029_8).

Expression cassettes and vectors containing a recombinant nucleic acid molecule sequence can be constructed and introduced into plants, in particular into corn, soybean or cotton plant cells in accordance with transformation methods and techniques known in the art. For example, *Agrobacterium*-mediated transformation is described in U.S. Patent Application Publications 2009/0138985A1 (soybean), 2008/0280361A1 (soybean), 2009/0142837A1 (corn), 2008/0282432 (cotton), 2008/0256667 (cotton), 2003/0110531 (wheat), 2001/0042257 A1 (sugar beet), U.S. Pat. No. 5,750,871 (canola), U.S. Pat. No. 7,026,528 (wheat), and U.S. Pat. No. 6,365,807 (rice), and in Arencibia et al. (1998) Transgenic Res. 7:213-222 (sugarcane) all of which are incorporated herein by reference in their entirety. Transformed cells can be regenerated into transformed plants that express TIC4029, TIC4029_1, and TIC4029-8 and demonstrate pesticidal activity through bioassays performed in the presence of Lepidopteran pest larvae using plant leaf disks obtained from the transformed plants. Plants can be derived from the plant cells by regeneration, seed, pollen, or meristem transformation techniques. Methods for transforming plants are known in the art.

As an alternative to traditional transformation methods, a DNA sequence, such as a transgene, expression cassette(s), etc., may be inserted or integrated into a specific site or locus within the genome of a plant or plant cell via site-directed integration. Recombinant DNA construct(s) and molecule(s) of this disclosure may thus include a donor template sequence comprising at least one transgene, expression cassette, or other DNA sequence for insertion into the genome of the plant or plant cell. Such donor template for site-directed integration may further include one or two homology arms flanking an insertion sequence (i.e., the sequence, transgene, cassette, etc., to be inserted into the plant genome). The recombinant DNA construct(s) of this disclosure may further comprise an expression cassette(s) encoding a site-specific nuclease and/or any associated protein(s) to carry out site-directed integration. These nuclease expressing cassette(s) may be present in the same molecule or vector as the donor template (in cis) or on a separate molecule or vector (in trans). Several methods for site-directed integration are known in the art involving different proteins (or complexes of proteins and/or guide RNA) that cut the genomic DNA to produce a double strand break (DSB) or nick at a desired genomic site or locus. Briefly as understood in the art, during the process of repairing the DSB or nick introduced by the nuclease enzyme, the donor template DNA may become integrated into the genome at the site of the DSB or nick. The presence of the homology arm(s) in the donor template may promote the adoption and targeting of the insertion sequence into the plant genome during the repair process through homologous recombination, although an insertion event may occur through non-homologous end joining (NHEJ). Examples of site-specific nucleases that may be used include zinc-finger nucleases, engineered or native meganucleases, TALE-endonucleases, and RNA-guided endonucleases (e.g., Cas9 or Cpf1). For methods using RNA-guided site-specific nucleases (e.g., Cas9 or Cpf1), the recombinant DNA construct(s) will also comprise a sequence encoding one or more guide RNAs to direct the nuclease to the desired site within the plant genome.

Recombinant nucleic acid molecule compositions that encode bacterial expressed TIC4029, TIC4029-1, and TIC4029-8, and the plant expressed TIC4029, TIC4029-1, and TIC4029_8 proteins can be expressed with recombinant DNA constructs in which a polynucleotide molecule with an ORF encoding the protein is operably linked to genetic expression elements such as a promoter and any other regulatory element necessary for expression in the system for which the construct is intended. Non-limiting examples include a plant-functional promoter operably linked to a TIC4029, TIC4029-1, or TIC4029_8 protein encoding sequence for expression of the protein in plants or a Bt-functional promoter operably linked to a TIC4029, TIC4029-1, or TIC4029_8 protein encoding sequence for expression of the protein in a Bt bacterium or other *Bacillus* species. Other elements can be operably linked to the TIC4029, TIC4029-1, or TIC4029_8 protein encoding sequence including, but not limited to, enhancers, introns, untranslated leaders, encoded protein immobilization tags (HIS-tag), translocation peptides (i.e., plastid transit peptides, signal peptides), polypeptide sequences for post-translational modifying enzymes, ribosomal binding sites, and RNAi target sites. Exemplary recombinant polynucleotide molecules provided herewith include, but are not limited to, a heterologous promoter operably linked to a polynucleotide such as SEQ ID NO:1, SEQ ID NO:3, SEQ ID NO:5, SEQ ID NO:6, SEQ ID NO:7, SEQ ID NO:8, and SEQ ID NO:9 that encodes the respective polypeptides or proteins having the amino acid sequence as set forth in SEQ ID NO:2 (encoded by SEQ ID NO:1 and SEQ ID NOs:5-7), SEQ ID NO:4 (encoded by SEQ ID NO:3 and SEQ ID NO:8), and SEQ ID NO:10 (encoded by SEQ ID NO:9). A heterologous promoter can also be operably linked to synthetic DNA coding sequences encoding a plastid targeted TIC4029, TIC4029-1, or TIC4029-8. The codons of a recombinant nucleic acid molecule encoding for proteins disclosed herein can be substituted by synonymous codons (known in the art as a silent substitution).

A recombinant DNA construct comprising TIC4029, TIC4029-1, or TIC4029_8 protein encoding sequences can further comprise a region of DNA that encodes for one or more insect inhibitory agents which can be configured to concomitantly express or co-express with a DNA sequence encoding a TIC4029, TIC4029-1, or TIC4029_8 protein, an insect inhibitory dsRNA molecule, or an ancillary protein. Ancillary proteins include, but are not limited to, co-factors, enzymes, binding-partners, or other agents that function to aid in the effectiveness of an insect inhibitory agent, for example, by aiding its expression, influencing its stability in plants, optimizing free energy for oligomerization, augmenting its toxicity, and increasing its spectrum of activity. An ancillary protein may facilitate the uptake of one or more insect inhibitory agents, for example, or potentiate the toxic effects of the toxic agent.

A recombinant DNA construct can be assembled so that all proteins or dsRNA molecules are expressed from one promoter or each protein or dsRNA molecule is under separate promoter control or some combination thereof. The proteins of this invention can be expressed from a multi-gene expression system in which one or more proteins of TIC4029, TIC4029-1, or TIC4029_8 are expressed from a common nucleotide segment which also contains other open reading frames and promoters, depending on the type of expression system selected. For example, a bacterial multi-gene expression system can utilize a single promoter to drive expression of multiply-linked/tandem open reading frames from within a single operon (i.e., polycistronic expression). In another example, a plant multi-gene expression system can utilize multiply-unlinked or linked expression cassettes, each cassette expressing a different protein or other agent such as one or more dsRNA molecules.

Recombinant polynucleotides or recombinant DNA constructs comprising a TIC4029, TIC4029-1, or TIC4029_8 protein encoding sequence can be delivered to host cells by vectors, e.g., a plasmid, baculovirus, synthetic chromosome, virion, cosmid, phagemid, phage, or viral vector. Such vectors can be used to achieve stable or transient expression of a TIC4029, TIC4029_1, or TIC4029_8 protein encoding sequence in a host cell, or subsequent expression of the encoded polypeptide. An exogenous recombinant polynucleotide or recombinant DNA construct that comprises a TIC4029, TIC4029-1, or TIC4029_8 protein encoding sequence and that is introduced into a host cell is referred in this application as a "transgene".

Transgenic bacteria, transgenic plant cells, transgenic plants, and transgenic plant parts that contain a recombinant polynucleotide that expresses any one or more of TIC4029, TIC4029-1, or TIC4029_8 or a related family toxin protein encoding sequence are provided herein. The term "bacterial cell" or "bacterium" can include, but is not limited to, an *Agrobacterium*, a *Bacillus*, an *Escherichia*, a *Salmonella*, a *Pseudomonas, Brevibacillus, Klebsiella, Erwinia*, or a *Rhizobium* cell. The term "plant cell" or "plant" can include but is not limited to a dicotyledonous or monocotyledonous plant. The term "plant cell" or "plant" can also include but is not limited to an alfalfa, banana, barley, bean, broccoli, cabbage, *brassica*, carrot, cassava, castor, cauliflower, celery, chickpea, Chinese cabbage, citrus, coconut, coffee, corn, clover, cotton, a cucurbit, cucumber, Douglas fir, eggplant, *eucalyptus*, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, *Radiata* pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell or plant. In certain embodiments, transgenic plants and transgenic plant parts regenerated from a transgenic plant cell are provided. In certain embodiments, the transgenic plants can be obtained from a transgenic seed, by cutting, snapping, grinding or otherwise disassociating the part from the plant. In certain embodiments, the plant part can be a seed, a boll, a leaf, a flower, a stem, a root, or any portion thereof, or a non-regenerable portion of a transgenic plant part. As used in this context, a "non-regenerable" portion of a transgenic plant part is a portion that cannot be induced to form a whole plant or that cannot be induced to form a whole plant that is capable of sexual and/or asexual reproduction. In certain embodiments, a non-regenerable portion of a plant part is a portion of a transgenic seed, boll, leaf, flower, stem, or root.

Methods of making transgenic plants that comprise insect, Lepidoptera-inhibitory amounts of a TIC4029, TIC4029_1, or TIC4029_8 protein are provided. Such plants can be made by introducing a recombinant polynucleotide that encodes any of the proteins provided in this application into a plant cell, and selecting a plant derived from said plant cell that expresses an insect, Lepidoptera-inhibitory amount of the protein. Plants can be derived from the plant cells by regeneration, seed, pollen, or meristem transformation techniques. Methods for transforming plants are known in the art.

Processed plant products, wherein the processed product comprises a detectable amount of a TIC4029, TIC4029-1, or TIC4029_8 protein, an insect inhibitory segment or fragment thereof, or any distinguishing portion thereof, are also disclosed herein. In certain embodiments, the processed product is selected from the group consisting of plant parts, plant biomass, oil, meal, sugar, animal feed, flour, flakes, bran, lint, hulls, processed seed, and seed. In certain embodiments, the processed product is non-regenerable. The plant product can comprise commodity or other products of commerce derived from a transgenic plant or transgenic plant part, where the commodity or other products can be tracked through commerce by detecting nucleotide segments or expressed RNA or proteins that encode or comprise distinguishing portions of a TIC4029, TIC4029_1, or TIC4029_8 protein.

Plants expressing the TIC4029, TIC4029_1, or TIC4029_8 proteins can be crossed by breeding with transgenic events expressing other toxin proteins and/or expressing other transgenic traits such as herbicide tolerance genes, genes conferring yield or stress tolerance traits, and the like, or such traits can be combined in a single stacked vector so that the traits are all linked.

As further described in the Examples, TIC4029, TIC4029_1, or TIC4029_8 protein-encoding sequences and sequences having a substantial percentage identity to TIC4029, TIC4029_1, or TIC4029-8, can be identified using methods known to those of ordinary skill in the art such as polymerase chain reaction (PCR), thermal amplification, and hybridization. For example, the proteins TIC4029, TIC4029-1, or TIC4029_8 can be used to produce antibodies that bind specifically to related proteins and can be used to screen for and to find other protein members that are closely related.

Furthermore, nucleotide sequences encoding the TIC4029, TIC4029_1, or TIC4029_8 toxin proteins can be used as probes and primers for screening to identify other members of the class using thermal-cycle or isothermal amplification and hybridization methods. For example, oligonucleotides derived from sequences as set forth in SEQ ID NOs:5-9 can be used to determine the presence or absence of a TIC4029, TIC4029_1, or TIC4029_8 transgene in a deoxyribonucleic acid sample derived from a commodity product. Given the sensitivity of certain nucleic acid detection methods that employ oligonucleotides, it is anticipated that oligonucleotides derived from sequences as set forth in SEQ ID NOs:5-9 can be used to detect a TIC4029, TIC4029_1, or TIC4029_8 transgene in commodity products derived from pooled sources where only a fraction of the commodity product is derived from a transgenic plant containing any of the transgenes. It is further recognized that such oligonucleotides may be used to introduce nucleotide sequence variation in each of SEQ ID NO:1, SEQ ID NO:3, SEQ ID NO:5, SEQ ID NO:6, SEQ ID NO:7, SEQ ID NO:8, and SEQ ID NO:9. Such "mutagenesis" oligonucleotides are useful for identification of TIC4029, TIC4029_1, and TIC4029_8 amino acid sequence variants exhibiting a range of insect inhibitory activity or varied expression in transgenic plant host cells.

Nucleotide sequence homologs, e.g., insecticidal proteins encoded by nucleotide sequences that hybridize to each or any of the sequences disclosed in this application under stringent hybridization conditions, are also an embodiment of the present invention. The invention also provides a method for detecting a first nucleotide sequence that hybridizes to a second nucleotide sequence, wherein the first nucleotide sequence (or its reverse complement sequence) encodes a pesticidal protein or pesticidal fragment thereof and hybridizes to the second nucleotide sequence. In such case, the second nucleotide sequence can be any of the nucleotide sequences presented as of SEQ ID NO:1, SEQ ID NO:3, SEQ ID NO:5, SEQ ID NO:6, SEQ ID NO:7, SEQ ID NO:8, or SEQ ID NO:9 under stringent hybridization conditions. Nucleotide coding sequences hybridize to one another under appropriate hybridization conditions, such as stringent hybridization conditions, and the proteins encoded by these nucleotide sequences cross react with antiserum raised against any one of the other proteins. Stringent hybridization conditions, as defined herein, comprise at least hybridization at 42° C. followed by two washes for five minutes each at room temperature with 2×SSC, 0.1% SDS, followed by two washes for thirty minutes each at 65° C. in 0.5×SSC, 0.1% SDS. Washes at even higher temperatures constitute even more stringent conditions, e.g., hybridization conditions of 68° C., followed by washing at 68° C., in 2×SSC containing 0.1% SDS.

One skilled in the art will recognize that, due to the redundancy of the genetic code, many other sequences are capable of encoding such related proteins, and those sequences, to the extent that they function to express pesticidal proteins either in *Bacillus* strains or in plant cells, are embodiments of the present invention, recognizing of course that many such redundant coding sequences will not hybridize under these conditions to the native *Bacillus* sequences encoding TIC4029, TIC4029-1, and TIC4029_8 variants. This application contemplates the use of these and other identification methods known to those of ordinary skill in the art, to identify TIC4029, TIC4029_1, and TIC4029_8 protein-encoding sequences and sequences having a substantial percentage identity to TIC4029, TIC4029-1, and TIC4029_8 protein-encoding sequences.

This disclosure also contemplates the use of molecular methods known in the art to engineer and clone commercially useful proteins comprising chimeras of proteins from pesticidal proteins; e.g., the chimeras may be assembled from segments of the TIC4029, TIC4029_1, or TIC4029_8 proteins to derive additional useful embodiments including assembly of segments of TIC4029, TIC4029_1, or TIC4029_8 proteins with segments of diverse proteins different from TIC4029, TIC4029_1, or TIC4029_8 proteins and related proteins. The TIC4029, TIC4029-1, or TIC4029_8 proteins may be subjected to alignment to each other and to other *Bacillus, Paenibacillus* or other pesticidal proteins (whether or not these are closely or distantly related phylogenetically), and segments of each such protein may be identified that are useful for substitution between the aligned proteins, resulting in the construction of chimeric proteins. Such chimeric proteins can be subjected to pest bioassay analysis and characterized for the presence or absence of increased bioactivity or expanded target pest spectrum compared to the parent proteins from which each such segment in the chimera has been derived. The pesticidal activity of the polypeptides may be further engineered for activity to a particular pest or to a broader spectrum of pests by swapping domains or segments with other proteins or by using directed evolution methods known in the art.

Methods of controlling insects, in particular Lepidoptera infestations of crop plants, with the TIC4029, TIC4029_1, or TIC4029_8 proteins are disclosed in this application. Such methods can comprise growing a plant comprising an insect- or Lepidoptera-inhibitory amount of a TIC4029, TIC4029_1, or TIC4029_8 toxin protein. In certain embodiments, such methods can further comprise any one or more of: (i) applying any composition comprising or encoding a TIC4029, TIC4029_1, or TIC4029_8 toxin protein to a plant or a seed that gives rise to a plant; and (ii) transforming a plant or a plant cell that gives rise to a plant with a polynucleotide encoding a TIC4029, TIC4029_1, or TIC4029_8 toxin protein. In general, it is contemplated that a TIC4029, TIC4029_1, or TIC4029_8 toxin protein can be provided in a composition, provided in a microorganism, or provided in a transgenic plant to confer insect inhibitory activity against Lepidopteran insects.

In certain embodiments, a recombinant nucleic acid molecule encoding TIC4029, TIC4029_1, or TIC4029_8 toxin proteins is the insecticidally active ingredient of an insect inhibitory composition prepared by culturing recombinant *Bacillus* or any other recombinant bacterial cell transformed to express a TIC4029, TIC4029_1, or TIC4029_8 toxin protein under conditions suitable to express the TIC4029, TIC4029_1, or TIC4029_8 toxin protein. Such a composition can be prepared by desiccation, lyophilization, homogenization, extraction, filtration, centrifugation, sedimentation, or concentration of a culture of such recombinant cells expressing/producing said recombinant polypeptide. Such a process can result in a *Bacillus* or other entomopathogenic bacterial cell extract, cell suspension, cell homogenate, cell lysate, cell supernatant, cell filtrate, or cell pellet. By obtaining the recombinant polypeptides so produced, a composition that includes the recombinant polypeptides can include bacterial cells, bacterial spores, and parasporal inclusion bodies and can be formulated for various uses, including as agricultural insect inhibitory spray products or as insect inhibitory formulations in diet bioassays.

In one embodiment, to reduce the likelihood of resistance development, an insect inhibitory composition comprising TIC4029, TIC4029_1, or TIC4029_8 protein can further comprise at least one additional polypeptide that exhibits insect inhibitory activity against the same Lepidopteran insect species, but which is different from the TIC4029, TIC4029_1, or TIC4029_8 toxin protein. Possible additional polypeptides for such a composition include an insect inhibitory protein and an insect inhibitory dsRNA molecule. One example for the use of such ribonucleotide sequences to control insect pests is described in Baum, et al. (U.S. Patent Publication 2006/0021087 A1). Such additional polypeptide for the control of Lepidopteran pests may be selected from the group consisting of an insect inhibitory protein, such as, but not limited to, Cry1A (U.S. Pat. No. 5,880,275), Cry1Ab, Cry1Ac, Cry1A.105, Cry1Ae, Cry1B (U.S. patent Publication Ser. No. 10/525,318), Cry1C (U.S. Pat. No. 6,033,874), Cry1D, Cry1Da and variants thereof, Cry1E, Cry1F, and Cry1A/F chimeras (U.S. Pat. Nos. 7,070,982; 6,962,705; and 6,713,063), Cry1G, Cry1H, Cry1I, Cry1J, Cry1K, Cry1L, Cry1-type chimeras such as, but not limited to, TIC836, TIC860, TIC867, TIC869, and TIC1100 (International Application Publication WO2016/061391 (A2)), TIC2160 (International Application Publication WO2016/061392(A2)), Cry2A, Cry2Ab (U.S. Pat. No. 7,064,249), Cry2Ae, Cry4B, Cry6, Cry7, Cry8, Cry9, Cry15, Cry43A, Cry43B, Cry51Aa1, ET66, TIC400, TIC800, TIC834, TIC1415, Vip3A, VIP3Ab, VIP3B, AXMI-001, AXMI-002, AXMI-030, AXMI-035, AND AXMI-045 (U.S. Patent Publication 2013-0117884 A1), AXMI-52, AXMI-58, AXMI-88, AXMI-97, AXMI-102, AXMI-112, AXMI-117, AXMI-100 (U.S. Patent Publication 2013-0310543 A1), AXMI-115, AXMI-113, AXMI-005 (U.S. Pat. Publication 2013-0104259 A1), AXMI-134 (U.S. Patent Publication 2013-0167264 A1), AXMI-150 (U.S. Patent Publication 2010-0160231 A1), AXMI-184 (U.S. Patent Publication 2010-0004176 A1), AXMI-196, AXMI-204, AXMI-207, AXMI-209 (U.S. Patent Publication 2011-0030096 A1), AXMI-218, AXMI-220 (U.S. Patent Publication 2014-0245491 A1), AXMI-221z, AXMI-222z, AXMI-223z, AXMI-224z, AXMI-225z (U.S. Patent Publication 2014-0196175 A1), AXMI-238 (U.S. Patent Publication 2014-0033363 A1), AXMI-270 (U.S. Patent Publication 2014-0223598 A1), AXMI-345 (U.S. Patent Publication 2014-0373195 A1), AXMI-335 (International Application Publication WO2013/134523(A2)), DIG-3 (U.S. Patent Publication 2013-0219570 A1), DIG-5 (U.S. Patent Publication 2010-0317569 A1), DIG-11 (U.S. Patent Publication 2010-0319093 A1), AfIP-1A and derivatives thereof (U.S. Patent Publication 2014-0033361 A1), AfIP-1B and derivatives thereof (U.S. Patent Publication 2014-0033361 A1), PIP-1APIP-1B (U.S. Patent Publication 2014-0007292 A1), PSEEN3174 (U.S. Patent Publication 2014-0007292 A1), AECFG-592740 (U.S. Patent Publication 2014-0007292 A1), Pput_1063 (U.S. Patent Publication 2014-0007292 A1), DIG-657 (International Application Publication WO2015/195594 A2), Pput_1064 (U.S. Patent Publication 2014-0007292 A1), GS-135 and derivatives thereof (U.S. Patent Publication 2012-0233726 A1), GS153 and derivatives thereof (U.S. Patent Publication 2012-0192310 A1), GS154 and derivatives thereof (U.S. Patent Publication 2012-0192310 A1), GS155 and derivatives thereof (U.S. Patent Publication 2012-0192310 A1), SEQ ID NO:2 and derivatives thereof as described in U.S. Patent Publication 2012-0167259 A1, SEQ ID NO:2 and derivatives thereof as described in U.S. Patent Publication 2012-0047606 A1, SEQ ID NO:2 and derivatives thereof as described in U.S. Patent Publication 2011-0154536 A1, SEQ ID NO:2 and derivatives thereof as described in U.S. Patent Publication 2011-0112013 A1, SEQ ID NO:2 and 4 and derivatives thereof as described in U.S. Patent Publication 2010-0192256 A1, SEQ ID NO:2 and derivatives thereof as described in U.S. Patent Publication 2010-0077507 A1, SEQ ID NO:2 and derivatives thereof as described in U.S. Patent Publication 2010-0077508 A1, SEQ ID NO:2 and derivatives thereof as described in U.S. Patent Publication 2009-0313721 A1, SEQ ID NO:2 or 4 and derivatives thereof as described in U.S. Patent Publication 2010-0269221 A1, SEQ ID NO:2 and derivatives thereof as described in U.S. Pat. No. 7,772,465 (B2), CF161_0085 and derivatives thereof as described in W02014/008054 A2, Lepidopteran toxic proteins and their derivatives as described in US Patent Publications US2008-0172762 A1, US2011-0055968 A1, and US2012-0117690 A1; SEQ ID NOs:2 or 4 and derivatives thereof as described in U.S. Pat. No. 7,510,878(B2), SEQ ID NOs:2 or 4 and derivatives thereof as described in U.S. Pat. No. 7,812,129 (B1); IPD110Aa and homologs (International Application Publication WO2019/178038 A2); TIC868 (U.S. Pat. No. 10,233,217), Cry1Da1_7 (U.S. Pat. No. 10,059,959), BCW003 (U.S. Pat. No. 10,703,782), TIC1100 (U.S. Pat. No. 10,494,408), TIC867 (U.S. Pat. No. 10,669,317), TIC867-23 (U.S. Pat. No. 10,611,806), TIC6757 (U.S. Pat. No. 10,155,960), TIC7941 (U.S. Patent Publication 2020-0229445 A1), fern toxins toxic to lepidopteran species such as those disclosed in U.S. Pat. No. 10,227,608, and the like.

In other embodiments, such composition/formulation can further comprise at least one additional polypeptide that exhibits insect inhibitory activity to an insect that is not inhibited by an otherwise insect inhibitory protein of the present invention to expand the spectrum of insect inhibition obtained. For example, for the control of Hemipteran pests, combinations of insect inhibitory proteins of the present invention can be used with Hemipteran-active proteins such as TIC1415 (US Patent Publication 2013-0097735 A1), TIC807 (U.S. Pat. No. 8,609,936), TIC834 (U.S. Patent Publication 2013-0269060 A1), AXMI-036 (U.S. Patent Publication 2010-0137216 A1), and AXMI-171 (U.S. Patent Publication 2013-0055469 A1). Further a polypeptide for the control of Coleopteran pests may be selected from the group consisting of an insect inhibitory protein, such as, but not limited to, Cry3Bb (U.S. Pat. No. 6,501,009), Cry1C variants, Cry3A variants, Cry3, Cry3B, Cry34/35, 5307, AXMI134 (U.S. Patent Publication 2013-0167264 A1) AXMI-184 (U.S. Patent Publication 2010-0004176 A1), AXMI-205 (U.S. Patent Publication 2014-0298538 A1), AXMI-207 (U.S. Patent Publication 2013-0303440 A1), AXMI-218, AXMI-220 (U.S. Patent Publication 20140245491A1), AXMI-221z, AXMI-223z (U.S. Patent Publication 2014-0196175 A1), AXMI-279 (U.S. Patent Publication 2014-0223599 A1), AXMI-R1 and variants thereof (U.S. Patent Publication 2010-0197592 A1, TIC407, TIC417, TIC431, TIC807, TIC853, TIC901, TIC1201, TIC3131, DIG-10 (U.S. Patent Publication 2010-0319092 A1), eHIPs (U.S. Patent Application Publication No. 2010/0017914), IP3 and variants thereof (U.S. Patent Publication 2012-0210462 A1). *Pseudomonas* toxin IDP072Aa (US Patent Application Publication No. 2014/055128), and ω̄-Hexatoxin-Hvla (U.S. Patent Application Publication US2014-0366227 A1).

Additional polypeptides for the control of Coleopteran, Lepidopteran, and Hemipteran insect pests, which can be combined with the insect inhibitory proteins of the TIC4029 family, can be found on the *Bacillus thuringiensis* toxin nomenclature website maintained by Neil Crickmore (on the world wide web at btnomenclature.info). Broadly, it is contemplated that any insect inhibitory protein known to those of skill in the art can be used in combination with the proteins of the TIC4029 family both in planta (combined through breeding or molecular stacking) or in a composition or formulation as a biopesticide or combination of biopesticides.

The possibility for insects to develop resistance to certain insecticides or insecticidal proteins has been documented in the art. One insect resistance management strategy is to employ transgenic crops that express two distinct insect inhibitory agents that operate through different modes of action. Therefore, any insects with resistance to either one of the insect inhibitory agents can be controlled by the other insect inhibitory agent. Another insect resistance management strategy employs the use of plants that are not protected to the targeted Lepidopteran pest species to provide a refuge for such unprotected plants. One particular example is described in U.S. Pat. No. 6,551,962, which is incorporated by reference in its entirety.

Other embodiments such as topically applied pesticidal chemistries that are designed for controlling pests that are also controlled by the proteins disclosed herein to be used with proteins in seed treatments, spray on, drip on, or wipe on formulations can be applied directly to the soil (a soil drench), applied to growing plants expressing the proteins disclosed herein, or formulated to be applied to seed containing one or more transgenes encoding one or more of the proteins disclosed. Such formulations for use in seed treatments can be applied with various stickers and tackifiers known in the art. Such formulations can contain pesticides that are synergistic in mode of action with the proteins disclosed, so that the formulation pesticides act through a different mode of action to control the same or similar pests that can be controlled by the proteins disclosed, or that such pesticides act to control pests within a broader host range or plant pest species that are not effectively controlled by the TIC4029, TIC4029_1, and TIC4029-8 pesticidal proteins.

The aforementioned composition/formulation can further comprise an agriculturally-acceptable carrier, such as a bait, a powder, dust, pellet, granule, spray, emulsion, a colloidal suspension, an aqueous solution, a *Bacillus* spore/crystal preparation, a seed treatment, a recombinant plant cell/plant tissue/seed/plant transformed to express one or more of the proteins, or bacterium transformed to express one or more of the proteins. Depending on the level of insect inhibitory or insecticidal inhibition inherent in the recombinant polypeptide and the level of formulation to be applied to a plant or diet assay, the composition/formulation can include various by weight amounts of the recombinant polypeptide, e.g. from 0.0001% to 0.001% to 0.01% to 1% to 99% by weight of the recombinant polypeptide.

In view of the foregoing, those of skill in the art should appreciate that changes can be made in the specific aspects which are disclosed and still obtain a like or similar result without departing from the spirit and scope of the invention. Thus, specific structural and functional details disclosed herein are not to be interpreted as limiting. It should be understood that the entire disclosure of each reference cited herein is incorporated within the disclosure of this application.

EXAMPLES

Example 1

Discovery, Cloning, and Expression of TIC4029 and the TIC4029 Variants TIC4029_1 and TIC4029_8

A sequence encoding a novel *Bacillus thuringiensis* pesticidal protein was identified, cloned, sequence confirmed, and tested in insect bioassay. The pesticidal protein, TIC4029 was isolated from Bt species EGBS0016 and represents a novel Cry1Ca-related protein. Bt strain EGBS0016 was initially identified as a spore forming, crystal and plasmid containing strain of Bt or Bt-like bacteria. DNA was isolated from EGBS0016 and sequenced. The assembled sequence was then analyzed bioinformatically. The TIC4029 protein was identified by pfam analysis to hits of endotoxin domains and identity to known Cry1Ca toxins. The full length TIC4029 protein amino acid sequence exhibits 86% identity to TIC1425 (U.S. Pat. No. 10,626,151. The insect toxin TIC1425 demonstrated activity against Cotton leaf worm (*Alabama argillacea*), European corn borer (*Ostrinia nubilalis*), Fall armyworm (*Spodoptera frugiperda*), Sugarcane borer (*Diatraea saccharalis*), and Southwestern corn borer (*Diatraea grandiosella*). Polymerase chain reaction (PCR) primers were designed to amplify a full-length copy of the coding region for TIC4029 from total genomic DNA isolated from the Bt species EGBS0016. The PCR amplicon also included the translational initiation and termination codons of the coding sequence.

The TIC4029 coding sequence was cloned using methods known in the art into a Bt expression vector in operable linkage with a Bt expressible promoter. Spore and soluble protein preparations were used in bioassay.

In addition, two truncated variants of TIC4029 were produced, TIC4029_1 and TIC4029-8. TIC4029_1 comprises a deletion of the protoxin domain and consists of amino acids 1-603 relative to TIC4029 (see FIGS. 1*a*-1*b*). The coding sequence of TIC4029_1 was synthesized and cloned into a bacterial expression vector in operable linkage with a Bt expressible promoter. Spore and soluble protein preparations were used in bioassay.

TIC4029_8 comprises deletions of the N-terminal amino acid segment and protoxin domain of TIC4029 and consists of amino acids 28-607 of TIC4029 (see FIGS. 1*a*-1*b*). In addition, an ATG codon was then introduced, replacing the arginine residue of TIC4029 at amino acid position 27 to enable translation initiation of the TIC4029_8 protein. The TIC4029_8 amino acid sequence represents the tryptic core of TIC4029. A sequence encoding TIC4029_8 was tested in planta for activity as described in Examples 4 and 5.

Example 2

TIC4029 and TIC4029_1 Exhibit Lepidopteran Toxic Activity in Insect Bioassay The pesticidal proteins TIC4029 and TIC4029_1 were expressed in Bt and assayed for toxicity to various species of Lepidoptera. TIC4029 was also assayed for toxicity to various species of Coleoptera, Hemiptera, and Diptera.

TIC4029 was assayed for toxicity to the Lepidopteran insect species Black cutworm (BCW, *Agrotis ipsilon*), Corn earworm (CEW, *Helicoverpa zea*, also known as Soybean podworm), European corn borer (ECB, *Ostrinia nubilalis*), Fall armyworm (FAW, *Spodoptera frugiperda*), Southern armyworm (SAW, *Spodoptera eridania*), Soybean looper (SBL, *Chrysodeixis includens*), Southwestern corn borer (SWC, *Diatraea grandiosella*), Sugarcane borer (SCB, *Diatraea saccharalis*), Sunflower looper (SFL, *Rachiplusia nu*), Tobacco budworm (TBW, *Heliothis virescens*), and Velvet bean caterpillar (VBC, *Anticarsia gemmatalis*); the Coleopteran species Colorado potato beetle (CPB, *Leptinotarsa decemlineata*) and Western Corn Rootworm (WCR, *Diabrotica virgifera*); the Hemipteran species Neotropical Brown Stink Bug (NBSB, *Euschistus heros*) and Western tarnished plant bug (WTP, *Lygus hesperus*); and the *Dipteran* species Yellow Fever Mosquito (YFM, *Aedes aegypti*). Bioassay using microbial host cell-derived protein samples containing TIC4029 exhibited activity against the Lepidopteran species BCW, CEW, ECB, FAW, SAW, SBL, SWC, SCB, SFL, TBW, and VBC. Activity was also observed against the *Dipteran* species YFM.

The bacterial encoded TIC4029_1 exhibited toxic activity against SBL and VBC. In addition, TIC4029 and TIC4029_1 exhibited toxic activity against Black armyworm (BAW, *Spodoptera cosmioides*).

Example 3

Synthetic Sequences Encoding TIC4029, TIC4029_1, or TIC4029_8 for Plant Expression Synthetic coding sequences were designed to encode TIC4029, TIC4029_1 or TIC4029_8 for expression of each of these toxins in plants.

The synthetic sequences were synthesized, according to methods generally described in U.S. Pat. No. 5,500,365, to avoid certain inimical problem sequences such as ATTTA and A/T rich plant polyadenylation sequences while substantially preserving the amino acid sequence of the native protein. TIC4029_PL-1 (SEQ ID NO:5), TIC4029_PL-2 (SEQ ID NO:6), and TIC4029_PL-3 (SEQ ID NO:7) each are different coding sequence constructs encoding TIC4029. One synthetic coding sequence was designed for TIC4029_1 (SEQ ID NO:8) and one synthetic coding sequence was designed for TIC4029_8 (SEQ ID NO:9).

These were transferred into plant transformation vectors using skills known in the art. The transformation vectors used to transform soybean plants comprised a first transgene cassette for expression of the applicable pesticidal protein including a plant functional constitutive promoter in operable linkage to a leader, the toxin coding sequence, an untranslated region (UTR), and a plant functional transcription termination and polyadenylation sequence. A second transgene cassette expressing a selectable marker, in this case spectinomycin resistance, was also included in the vector. The transformation vectors used to transform corn plants included a first transgene cassette for expression of the applicable pesticidal protein and included a plant functional constitutive promoter in operable linkage to a leader sequence, an intron sequence, an untranslated region (UTR) including a transcription and translation termination sequence and a plant polyadenylation sequence and included a second transgene cassette encoding glyphosate tolerance for selection of transformed plant cells.

Example 4

TIC4029, TIC4029_1, and TIC4029_8 Demonstrate Lepidopteran Toxic Activity in Stably Transformed Soybean Plants Binary plant transformation vectors comprising transgene cassettes designed to express the pesticidal proteins TIC4029, TIC4029_1, and TIC4029_8 were constructed using methods known in the art. The resulting vectors were used to stably transform soybean plants with expression cassettes encoding these toxin proteins. Plant tissues expressing these toxin proteins were used in insect bioassay against various Lepidopteran insect species as described herein.

Soybean plant cells were transformed with the binary transformation vectors using an *Agrobacterium*-mediated transformation method. The transformed cells were induced to form plants by methods known in the art. Bioassays using plant leaf disks obtained from the transformed plants were performed similar to methods described in U.S. Pat. No. 8,344,207. A single freshly hatched neonate larvae less than one day old was placed on each leaf disc sample and allowed to feed for approximately four days. A non-transformed soybean plant was used as a negative control. Multiple $R_0$ single-copy insertion events arising from each binary vector were assessed against Southern armyworm (SAW, *Spodoptera eridania*), Soybean looper (SBL, *Chrysodeixis includens*), Soybean pod worm (SPW, *Helicoverpa zea*), and Velvet bean caterpillar (VBC, *Anticarsia gemmatalis*). An efficacy rating score (efficacy score) which ranged from 0 to 3 was assigned to each event based upon the percent leaf damage in the bioassay for each event and the percentage of events that shared the lowest percent range of damage (Penetrance) as shown in Table 2. A rating score of 3 represents the most efficacious effect of toxicity based on feeding on that particular sample. A rating score of 2 represents that the sample on which the larvae was feeding exhibited suppression of growth, molting, or caused morbidity and often, mortality.

TABLE 2

Standards for Efficacy rating score, Leaf Damage Percentage, and Penetrance for Soybean Plants Expressing Toxin.

| Efficacy score | Percent Leaf Damage | Penetrance |
|---|---|---|
| 0 | >50% | ≥80% |
| 1 | <50% | ≥20% |
| 2 | <30% | ≥20% |
| 3 | ≤10% | ≥50% |

Table 3 illustrates the efficacy scores for $R_0$ soybean plants expressing TIC4029, TIC4029_1, and TIC4029_8. The numbers in parenthesis represent the number of events that shared the lowest percent range of damage/total number of events assayed, and "NT" indicates not tested. For TIC4029 and TIC4029_1, multiple constructs were used to transform plants, each comprising different expression elements.

TABLE 3

Efficacy scores for $R_0$ soybean plants expressing TIC4029, TIC4029_1, and TIC4029_8.

| Toxin | Construct | Coding Sequence | SEQ ID NO: | SAW | SBL | SPW | VBC |
|---|---|---|---|---|---|---|---|
| | | | | Efficacy Rating Score | | | |
| TIC4029 | 1 | TIC4029PL-1 | 5 | 3 (17/20) | 3 (19/20) | 0 (18/20) | 2 (7/20) |
| TIC4029 | 1 | TIC4029PL-1 | 5 | 2 (14/15) | 3 (14/15) | 0 (15/15) | 0 (15/15) |
| TIC4029 | 1 | TIC4029PL-1 | 5 | 3 (12/14) | 3 (13/14) | 0 (14/14) | NT |
| TIC4029 | 2 | TIC4029PL-1 | 5 | 2 (8/13) | 3 (12/13) | 0 (12/13) | NT |
| TIC4029 | 3 | TIC4029PL-1 | 5 | 3 (12/14) | 3 (13/14) | 0 (14/14) | NT |
| TIC4029 | 4 | TIC4029PL-1 | 5 | 0 (19/19) | 2 (13/19) | 0 (19/19) | NT |
| TIC4029 | 5 | TIC4029PL-1 | 5 | 0 (12/14) | 3 (12/14) | 0 (14/14) | NT |
| TIC4029 | 6 | TIC4029PL-1 | 5 | 2 (13/20) | 3 (18/20) | 0 (20/20) | NT |
| TIC4029 | 7 | TIC4029PL-1 | 5 | 3 (18/20) | 3 (20/20) | 0 (20/20) | 2 (5/20) |
| TIC4029 | 8 | TIC4029PL-1 | 5 | 2 (14/20) | 3 (19/20) | 0 (20/20) | NT |
| TIC4029_1 | 1 | TIC4029_1PL | 8 | 3 (8/14) | 3 (11/14) | 0 (14/14) | 2 (8/14) |
| TIC4029_1 | 1 | TIC4029_1PL | 8 | 3 (17/20) | 3 (19/20) | 0 (20/20) | 3 (19/20) |
| TIC4029_1 | 1 | TIC4029_1PL | 8 | 3 (19/20) | 3 (20/20) | 0 (20/20) | NT |
| TIC4029_1 | 2 | TIC4029_1PL | 8 | NT | 3 (15/16) | 0 (16/16) | NT |
| TIC4029_1 | 3 | TIC4029_1PL | 8 | 2 (5/12) | 3 (12/12) | 0 (12/12) | NT |
| TIC4029_1 | 4 | TIC4029_1PL | 8 | 2 (4/16) | 3 (13/16) | 0 (16/16) | NT |
| TIC4029_1 | 5 | TIC4029_1PL | 8 | 1(6/10) | 3 (8/10) | 0 (10/10) | NT |
| TIC4029_1 | 6 | TIC4029_1PL | 8 | 3 (16/18) | 3 (17/18) | 0 (18/18) | NT |
| TIC4029_1 | 7 | TIC4029_1PL | 8 | 3 (14/17) | 3 (17/17) | 0 (17/17) | 2 (10/17) |
| TIC4029_8 | 1 | TIC4029_8PL | 9 | 3 (14/16) | 3 (16/16) | 0 (16/16) | NT |
| TIC4029_8 | 1 | TIC4029_8PL | 9 | 3 (13/14) | 3 (11/14) | NT | 3 (12/14) |

As can be seen in Table 3, $R_0$ 9 of the 10 constructs used to express TIC4029 in stably transformed soybean were efficacious against SBL. All 9 constructs used to express TIC4029_1 and both constructs used to express TIC4029_8 in stably transformed soybean were efficacious against SBL. Four of the constructs used to express TIC4029PL-1 were efficacious against SAW, while 4 other constructs provided suppression of SAW.

Selected $R_0$ soybean plants expressing TIC4029, TIC4029_1, and TIC4029_8 were allowed to self-pollinate and produce $R_1$ seed. The $R_1$ seed was used to grow $R_1$ plants. $R_1$ plants homozygous for the pesticidal protein expression cassette were selected for leaf disc bioassay against SAW, SBL, SPW and VBC. Table 4 shows the efficacy rating scores for $R_1$ homozygous plants expressing TIC4029, TIC4029_1, and TIC4029_8.

TABLE 4

Efficacy rating scores for $R_1$ soybean plants expressing TIC4029 and TIC4029_1 amino acid variants.

| Toxin | Construct | Coding Sequence | SEQ ID NO: | SAW | SBL | SPW | VBC |
|---|---|---|---|---|---|---|---|
| TIC4029 | Construct-1 | TIC4029PL-1 | 5 | 3 (10/10) | 3 (10/10) | 0 (10/10) | 1 (8/10) |
| TIC4029 | Construct-1 | TIC4029PL-1 | 5 | 3 (8/11) | NT | NT | NT |
| TIC4029 | Construct-2 | TIC4029PL-1 | 5 | 3 (5/7) | NT | NT | 1 (5/7) |
| TIC4029 | Construct-3 | TIC4029PL-1 | 5 | 3 (8/8) | NT | NT | 1 (6/8) |
| TIC4029 | Construct-4 | TIC4029PL-1 | 5 | 0 (7/7) | 3 (6/7) | NT | 0 (7/7) |
| TIC4029 | Construct-5 | TIC4029PL-1 | 5 | 3 (4/7) | NT | NT | 0 (7/7) |
| TIC4029 | Construct-6 | TIC4029PL-1 | 5 | 3 (5/9) | 3 (7/9) | NT | 0 (9/9) |
| TIC4029 | Construct-7 | TIC4029PL-1 | 5 | 3 (10/10) | 3 (10/10) | NT | 0 (6/10) |
| TIC4029 | Construct-8 | TIC4029PL-1 | 5 | 3 (7/9) | 3 (7/9) | NT | 0 (8/9) |
| TIC4029_1 | Construct-1 | TIC4029_1PL | 8 | 3 (8/10) | NT | NT | 3 (8/10) |
| TIC4029_1 | Construct-1 | TIC4029_1PL | 8 | 3 (11/11) | NT | NT | NT |
| TIC4029_1 | Construct-2 | TIC4029_1PL | 8 | 3 (7/8) | NT | NT | 3 (5/8) |
| TIC4029_1 | Construct-3 | TIC4029_1PL | 8 | 3 (9/9) | NT | NT | 3 (9/9) |
| TIC4029_1 | Construct-4 | TIC4029_1PL | 8 | 3 (6/9) | NT | NT | 0 (7/9) |
| TIC4029_1 | Construct-5 | TIC4029_1PL | 8 | 3 (3/5) | NT | NT | 1 (3/5) |
| TIC4029_1 | Construct-6 | TIC4029_1PL | 8 | 3 (11/11) | NT | NT | 3 (9/11) |
| TIC4029_1 | Construct-7 | TIC4029_1PL | 8 | 3 (7/8) | NT | NT | 3 (7/8) |
| TIC4029_8 | Construct-1 | TIC4029_8PL | 10 | 3 (8/9) | NT | NT | NT |

As can be seen in Table 4, $R_1$ homozygous plants derived from 5 selected constructs expressing TIC4029 were efficacious against SBL. $R_1$ homozygous plants derived from 8 selected constructs expressing TIC4029 were efficacious against SAW. $R_1$ homozygous plants derived from 8 selected constructs expressing TIC4029_1 and 1 selected construct expressing TIC4029_8 were efficacious against SAW.

In one trial, $R_1$ homozygous plants derived from transformation with Construct-1 and Construct-3 expressing TIC4029 were assayed using leaf disc assays as described above against Bean shoot moth (*Crocidosema aporema*), resulting in 50% to 100% mortality. TIC4029 is active against Bean shoot moth (*Crocidosema aporema*). $R_1$ homozygous plants derived from transformation with Construct-3 expressing TIC4029 were assayed against Cry1Ac-resistant Sunflower looper (SFL, *Rachiplusia nu*) and were highly efficacious against Cry1Ac-resistant SFL.

Example 5

TIC4029, TIC4029_1, and TIC4029_8 Demonstrate Activity Against Southwestern Corn Borer in Stably Transformed Corn Plants Binary plant transformation vectors comprising transgene cassettes designed to express the TIC4029, TIC4029_1, and TIC4029_8 pesticidal proteins were cloned using methods known in the art. The resulting vectors were used to stably transform corn plants. Tissues were harvested from the transformants and used in insect bioassay against various Lepidopteran insect species.

Corn plants were transformed with the binary transformation vectors as described in Example 3 using an *Agrobacterium*-mediated transformation method. The transformed cells were induced to form plants by methods known in the art. Bioassays using plant leaf disks were performed analogous to those described in U.S. Pat. No. 8,344,207. A single freshly hatched neonate larvae less than one day old was placed on each leaf disc sample and allowed to feed for approximately four days. A non-transformed corn plant was used to obtain tissue to be used as a negative control. Multiple transformation $R_0$ single-copy insertion events from each binary vector were assessed against Southwestern corn borer (SWC, *Diatraea grandiosella*). An efficacy rating score which ranged from 0 to 3 was assigned to each event based upon the percent leaf damage in the bioassay for each event and the percent events that shared the lowest percent range of damage (Penetrance) as shown in Table 2 of Example 3.

Table 5 below shows the efficacy scores for $R_0$ stably transformed corn plants expressing TIC4029, TIC4029_1, and TIC4029_8. The numbers in parenthesis represent the number of events that shared the lowest percent range of damage/total number of events assayed. For TIC4029, two constructs were used to transform plants, each comprising different coding sequences encoding TIC4029, but identical expression elements.

TABLE 5

Efficacy rating scores for $R_0$ corn plants expressing TIC4029, TIC4029_1, and TIC4029_8 against Southwestern corn borer.

| Toxin | Construct | Coding Sequence | SEQ ID NO: | SWC |
|---|---|---|---|---|
| TIC4029 | Construct-1 | TIC4029PL-1 | 5 | 1 (2/3) |
| TIC4029 | Construct-1 | TIC4029PL-1 | 5 | 0 (37/40) |
| TIC4029 | Construct-1 | TIC4029PL-1 | 5 | 2 (11/31) |
| TIC4029 | Construct-2 | TIC4029PL-2 | 6 | 3 (20/25) |
| TIC4029_1 | Construct-1 | TIC4029_1PL | 8 | 2 (12/40) |
| TIC4029_1 | Construct-1 | TIC4029_1PL | 8 | 3 (26/40) |
| TIC4029_8 | Construct-1 | TIC4029_8PL | 10 | 3 (13/18) |

As can be seen in Table 5, $R_0$ single-copy corn plants expressing TIC4029 transformed with Construct-2 which comprised the TIC4029 coding sequence, TIC4029-2 (SEQ ID NO:6) and TIC4029_1 and TIC4029_8 were efficacious against SWC. Expression levels of TIC4029 from the coding sequence TIC4029PL-1 were much lower than the expression levels observed for TIC4029PL-2 which were likely responsible for the lower efficacy scores derived from constructs comprising the TIC4029PL-1 coding sequence. A selected $R_0$ single-copy plant transformed with Construct-2 expressing TIC4029 using the coding sequence, TIC4029PL-2 was allowed crossed with a non-transformed elite variety of corn. Heterozygous $F_1$ events derived from this cross were assayed against SWC. These heterozygous $F_1$ events were efficacious against SWC.

Example 6

TIC4029 is Efficacious Against Soybean Looper, Sunflower Looper, and Velvet Bean Caterpillar and Provides Suppression of Southern Armyworm in Screenhouse Trials Soybean plants expressing TIC4029 were assayed for protection against selected insect pest species in screenhouse trials in the United States and in Argentina.

In the United States during the 2019 growth season, soybean plants expressing TIC4029 were assayed in screenhouse trials against Southern armyworm (SAW, *Spodoptera eridania*), Soybean looper (SBL, *Chrysodeixis includens*), Soybean podworm (SPW, *Helicoverpa zea*), and Velvet bean caterpillar (VBC, *Anticarsia gemmatalis*) in several locations. Screenhouse trials were conducted in Jerseyville, IL against SAW and SBL, in Union City, TN against SBL, and against VBC and SPW in Waterman, IL The events were evaluated using a randomized complete clock design. Each event plot was planted in a single six (6) foot row with approximately eight (8) seeds per foot. Each event had three (3) reps; hence each event was represented in the screenhouse by three (3) separate plots, randomly located within the screenhouse. A non-transformed event served as a negative control whose plots were also randomly assigned to locations within the screenhouse.

Infestation of SPW and VBC was accomplished using adult moths. The insects were reared to pupae in an insectary at Union City, TN in adult emergence cages, and maintained in climate-controlled incubators. The insects were shipped to Waterman and Jerseyville, IL for release in the screenhouse. Approximately one thousand two hundred (1,200) to two thousand (2,000) adults were used for each release in the screenhouses. For SPW, adults were released in the screenhouse each week from the R1 to R2 stage of soybean development. With respect to VBC, adults were released in the screenhouse bi-weekly between the developmental stages of V4 to R3. Approximately one thousand two hundred (1,200) to two thousand (2,000) adults were released each time in the screenhouses. Adult moths required continuous access to a ten percent (10%) sucrose solution for normal longevity and fecundity. Plastic food containers were filled with absorbent cotton and then the sugar solution was poured into the container to completely saturate the cotton. The sugar solution was replenished daily until adult activity subsided which was usually around two weeks after the final release of adults.

For SAW infestation, a. direct egg infestation was used since this insect does not oviposit preferentially or uniformly on soybean. Approximately two hundred fifty thousand (250,000) to three hundred twenty thousand (320,000) eggs were used for each infestation, and applied bi-weekly from R1 to R3 stage of development. Pieces of paper containing equal numbers of SAW eggs were attached to plants by folding the paper over a sturdy leaf petiole in the upper canopy and stapling the paper together securely. One (1) paper was placed on a plant within one (1) foot of the front end of the plot, a second paper was placed on a plant in the middle of the plot, and a third paper was placed on a plant within one (1) foot of the back end of the plot.

The percent defoliation was assessed at different stages of plant development. For SAW, percent defoliation was assessed at R2.8, R4.1, R4.8, and R6.0 developmental stage at Jerseyville, IL. For SBL, percent defoliation was determined at R2.0, R3.1, R4.2, and R5.5 developmental stage at Union City, TN, and at R5.4 and R5.8 developmental stage at Jerseyville, IL For VBC, percent defoliation was assessed at R3.9, R5.0, and R5.4 developmental stage at Waterman, IL For SPW, percent defoliation was assessed at R4.1, R4.7, R5.4, and R5.8 developmental stage at Waterman, IL A maximum percent defoliation was derived from the highest percent defoliation observed amongst the different developmental stages for each insect. Table 6 below shows the average maximum percent defoliation for plants expressing TIC4029 for SAW, SBL, and VBC. The average maximum percent defoliation for SPW was similar to the negative control and is not presented in Table 6.

TABLE 6

Average maximum percent defoliation for soybean plants expressing TIC4029 in United States screenhouse trials.

| | SAW | | SBL | | VBC | |
|---|---|---|---|---|---|---|
| Location | Neg | TIC4029 | Neg | TIC4029 | Neg | TIC4029 |
| Jerseyville, IL | 56.5 | 12.5 | 25.0 | 0.0 | | |
| Union City, TN | | | 71.5 | 0.2 | | |
| Waterman, IL | | | | | 50.3 | 0.8 |

As can be seen in Table 6, plants expressing TIC4029 were efficacious in controlling SBL and VBC; and demonstrated suppression of SAW.

Screenhouse trials were also conducted at two locations in Argentina, Fran Luis, BA and Pergamino, BA during the 2019-2020 growing season for soybean plants expressing TIC4029. Screenhouse trials were conducted in a similar manner as those in the United States in 2017. Each plot in the screenhouse comprised a row of forty-two (42) seeds in a two (2) meter row. Each event was represented by three (3) representative samples randomly located within the screenhouse. Screenhouse trials were conducted against the lepidopteran insect pests, Soybean looper (SBL, *Chrysodeixis includens*), Velvet bean caterpillar (VBC, *Anticarsia gemmatalis*), South American podworm (SAPW, *Helicoverpa gelotopoeon*), Sunflower looper (SFL, *Rachiplusia nu*), and Black armyworm (BAW, *Spodoptera cosmioides*).

The percent defoliation was assessed at different stages of plant development. For SBL, percent defoliation was assessed at R5.0, R5.5, and R6.0 developmental stage at Fran Luis, BA and at R4.0, R5.1, and R5.6 developmental stage at Pergamino, BA. For VBC, percent defoliation was assessed at R5.5, R6.0, and R6.5 developmental stage at Fran Luis, BA and at R5.0, R5.6, and R6.0 developmental stage at Pergamino, BA. For SFL, percent defoliation was assessed at R5.0, R5.3, R5.5, and R6.0 developmental stage at Fran Luis, BA and at R3.0, R4.0, R5.2, and R6.2 developmental stage at Pergamino, BA. For SAPW, percent defoliation was assessed at R4.4, R5.1, R5.5, and R6.0 developmental stage at Fran Luis, BA and at R3.0, R4.0, R5.1, and R6.2 developmental stage at Pergamino, BA. For BAW, percent defoliation was assessed at R3.0, R5.0, R5.5, and R6.0 developmental stage at Fran Luis, BA and at R5.1, R5.4, and R6.0 developmental stage at Pergamino, BA. A maximum percent defoliation was determined as described previously in this Example for each of the insect pests in each location. Table 7 below shows the average maximum percent defoliation for plants expressing TIC4029. The maximum percent defoliation for SAPW and BAW were equal to the controls and are not included in Table 7.

TABLE 7

Average maximum percent defoliation for soybean plants expressing TIC4029 in Argentina screenhouse trials.

| Insect | Transgene | Fran Luis, BA, ARG | Pergamino, BA, ARG |
|---|---|---|---|
| SBL | Neg | 82.5 | 62.0 |
| | TIC4029 | 3.1 | 5.2 |
| VBC | Neg | 32.0 | 88.0 |
| | TIC4029 | 4.5 | 6.0 |
| SFL | Neg | 47.2 | 37.6 |
| | TIC4029 | 5.5 | 4.3 |

As can be seen in Table 7, soybean plants expressing TIC4029 were efficacious against SBL, VBC, and SFL.

TIC4029 is efficacious against SBL, VBC, and SFL; and provides suppression of SAW.

All of the compositions disclosed and claimed herein can be made and executed without undue experimentation in light of the present disclosure. While the compositions of this invention have been described in terms of the foregoing illustrative embodiments, it will be apparent to those of skill in the art that variations, changes, modifications, and alterations may be applied to the composition described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

All publications and published patent documents cited in the specification are incorporated herein by reference to the same extent as if each individual publication or patent application was specifically and individually indicated to be incorporated by reference.

What is claimed is:

1. A recombinant nucleic acid molecule comprising a heterologous promoter operably linked to a polynucleotide encoding a pesticidal protein, wherein:

a. said pesticidal protein comprises the amino acid sequence as set forth in SEQ ID NO:2, SEQ ID NO:4, or SEQ ID NO:10; or b. said pesticidal protein comprises an amino acid sequence having at least 95% identity to the amino acid sequence as set forth in SEQ ID NO:2, SEQ ID NO:4, or SEQ ID NO:10.

2. The recombinant nucleic acid molecule of claim 1, wherein the recombinant nucleic acid molecule is in operable linkage with a vector, and said vector is selected from the group consisting of a plasmid, phagemid, bacmid, cosmid, and a bacterial or yeast artificial chromosome.

3. A host cell comprising the recombinant nucleic acid molecule of claim 1, wherein said host cell is selected from the group consisting of a bacterial cell and a plant cell.

4. The host cell of claim 3, wherein said bacterial cell is from a genus of bacteria selected from the group consisting of: *Agrobacterium, Rhizobium, Bacillus, Brevibacillus, Escherichia, Pseudomonas, Klebsiella, Pantoea*, and *Erwinia*.

5. The host cell of claim 4, wherein said *Bacillus* is a *Bacillus cereus* or *Bacillus thuringiensis*, said *Brevibacillus* is a *Brevibacillus laterosporus*, and said *Escherichia* is *Escherichia coli*.

6. The host cell of claim 3, wherein said plant cell is a dicotyledonous or a monocotyledonous plant cell.

7. The host cell of claim 6, wherein said plant cell is selected from the group consisting of an alfalfa, banana, barley, bean, broccoli, cabbage, *brassica*, carrot, cassava, castor, cauliflower, celery, chickpea, Chinese cabbage, citrus, coconut, coffee, corn, clover, cotton, a cucurbit, cucumber, Douglas fir, eggplant, *eucalyptus*, flax, garlic, grape, hops, leek, lettuce, Loblolly pine, millets, melons, nut, oat, olive, onion, ornamental, palm, pasture grass, pea, peanut, pepper, pigeon pea, pine, potato, poplar, pumpkin, *Radiata* pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell.

8. The recombinant nucleic acid molecule of claim 1, wherein said protein exhibits activity against a Lepidopteran insect.

9. The recombinant nucleic acid molecule of claim 8, wherein said Lepidopteran insect is selected from the group consisting of: Bean shoot moth (*Crocidosema aporema*), Black armyworm (*Spodoptera* cosmioides), Black cutworm (*Agrotis ipsilon*), Corn earworm (*Helicoverpa zea*), European corn borer (*Ostrinia nubilalis*), Fall armyworm (*Spodoptera frugiperda*), Southern armyworm (*Spodoptera eridania*), Soybean looper (*Chrysodeixis includens*), Southwestern corn borer (*Diatraea grandiosella*), Sugarcane borer (*Diatraea* saccharalis), Sunflower looper (*Rachiplusia nu*), Tobacco budworm (*Heliothis virescens*), and Velvet bean caterpillar (*Anticarsia gemmatalis*).

10. A plant comprising the recombinant nucleic acid molecule of claim 1, or part thereof.

11. The plant of claim 10, wherein said plant is a monocot plant or a dicot plant, or a part thereof.

12. The plant of claim 10, wherein the plant is selected from the group consisting of an alfalfa, banana, barley, bean, broccoli, cabbage, *brassica*, carrot, cassava, castor, cauliflower, celery, chickpea, Chinese cabbage, citrus, coconut, coffee, corn, clover, cotton, a cucurbit, cucumber, Douglas fir, eggplant, *eucalyptus*, flax, garlic, grape, hops, leek, lettuce, Loblolly pine, millets, melons, nut, oat, olive, onion, ornamental, palm, pasture grass, pea, peanut, pepper, pigeon pea, pine, potato, poplar, pumpkin, *Radiata* pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat.

13. The plant of claim 10, wherein the part thereof is a seed, and wherein said seed comprises said recombinant nucleic acid molecule.

14. An insect inhibitory composition comprising the recombinant nucleic acid molecule of claim 1.

15. The insect inhibitory composition of claim 14, further comprising a nucleotide sequence encoding at least one other pesticidal agent that is different from said pesticidal protein.

16. The insect inhibitory composition of claim 15, wherein said at least one other pesticidal agent is selected from the group consisting of an insect inhibitory protein, an insect inhibitory dsRNA molecule, a chemical molecule, and an ancillary protein, and wherein said at least one other pesticidal agent is toxic to the same pest as the pesticidal protein.

17. The insect inhibitory composition of claim 15, wherein said at least one other pesticidal agent exhibits activity against one or more pest species of the orders Lepidoptera, Coleoptera, or Hemiptera.

18. The insect inhibitory composition of claim 15, wherein said at least one other pesticidal protein is selected from the group consisting of a Cry1A, Cry1Ab, Cry1Ac, Cry1A.105, Cry1Ae, Cry1B, Cry1C, Cry1C variants, Cry1D, Cry1E, Cry1F, Cry1A/F chimeras, Cry1G, Cry1H, Cry1I, Cry1J, Cry1K, Cry1L, Cry2A, Cry2Ab, Cry2Ae, Cry3, Cry3A, Cry3B, Cry4B, Cry6, Cry7, Cry8, Cry9, Cry15, Cry34, Cry35, Cry43A, Cry43B, Cry51Aa1, ET29, ET33, ET34, ET35, ET66, ET70, TIC400, TIC407, TIC417, TIC431, TIC800, TIC807, TIC834, TIC853, TIC900, TIC901, TIC1201, TIC1415, TIC2160, TIC3131, TIC836, TIC860, TIC867, TIC869, TIC1100, VIP3A, VIP3B, VIP3Ab, AXMI-88, AXMI-97, AXMI-102, AXMI-112, AXMI-117, AXMI-100, AXMI-115, AXMI-113, and AXMI-005, AXMI134, AXMI-150, AXMI-171, AXMI-184, AXMI-196, AXMI-204, AXMI-207, AXMI-209, AXMI-205, AXMI-218, AXMI-220, AXMI-221z, AXMI-222z, AXMI-223z, AXMI-224z and AXMI-225z, AXMI-238, AXMI-270, AXMI-279, AXMI-345, AXMI-335, AXMI-R1, IP3, DIG-3, DIG-5, DIG-10, DIG-657, DIG-11 protein, IPD102Aa and homologs thereof, IPD110Aa and homologs thereof, TIC868, Cry1Da1_7, BCW003, TIC1100, TIC867, TIC867_23, TIC6757, TIC7941, IDP072Aa, TIC5290, TIC3668, TIC3669, TIC3670, IPD103 and homologs thereof, PIP-50 and PIP-65 and homologs thereof, PIP-83 and homologs thereof, and Cry1B.34.

19. The insect inhibitory composition of claim 14, comprising a plant cell that expresses an insecticidally effective amount of the pesticidal protein.

20. A commodity product produced from the plant, or part thereof, of claim 10, wherein the commodity product comprises a detectable amount of said recombinant nucleic acid molecule or said pesticidal protein.

21. The commodity product of claim 20, selected from the group consisting of commodity corn bagged by a grain handler, corn flakes, corn cakes, corn flour, corn meal, corn syrup, corn silage, corn starch, corn cereal, and corresponding soybean, rice, wheat, sorghum, pigeon pea, peanut, fruit, melon, and vegetable commodity products including juices, concentrates, jams, jellies, marmalades, whole or processed cotton seed, lint, seeds and plant parts processed for feed or food, fiber, paper, biomasses, whole or processed soybean seed, soybean protein, soybean meal, soybean flour, soybean flakes, soybean bran, soybean milk, soybean cheese, soybean wine, animal feed comprising soybean, paper comprising soybean, cream comprising soybean, soybean biomass, and fuel products produced using soybean plants and soybean plant parts.

22. A method of producing progeny seed comprising the recombinant nucleic acid molecule of claim 1, said method comprising:

a. planting a first seed comprising said recombinant nucleic acid molecule;

b. growing a plant from the seed of step a.; and c. harvesting said progeny seed from the plant, wherein said harvested seed comprise said recombinant nucleic acid molecule.

23. A plant resistant to insect infestation, wherein the cells of said plant comprise the recombinant nucleic acid molecule of claim 1.

24. A method for controlling a Lepidopteran species pest or pest infestation, said method comprising contacting the pest with the recombinant nucleic acid molecule of claim 1 and an insecticidally effective amount of the pesticidal protein encoded by the recombinant nucleic acid molecule.

25. A method of detecting the presence of the recombinant nucleic acid molecule of claim 1 in a sample comprising plant genomic DNA, comprising:

a. contacting said sample with a nucleic acid probe that hybridizes with said polynucleotide, and does not hybridize with genomic DNA from an otherwise isogenic plant that does not comprise said polynucleotide, wherein said probe is homologous or complementary to the nucleic acid sequence as set forth in SEQ ID NO:5, SEQ ID NO:6, SEQ ID NO:7, SEQ ID NO:8; or SEQ ID NO:9;

b. hybridizing said probe with said polynucleotide; and c. detecting hybridization of said probe with said with said polynucleotide; wherein detecting said hybridization confirms the presence of the recombinant nucleic acid molecule in said sample.

26. A plant cell comprising a protein comprising the amino acid sequence as set forth in SEQ ID NO:2, SEQ ID NO:4, or SEQ ID NO:10.

27. The recombinant nucleic acid molecule of claim 1, wherein said pesticidal protein comprises an amino acid sequence having at least 97% identity to the amino acid sequence as set forth in SEQ ID NO:2, SEQ ID NO:4, or SEQ ID NO:10.

28. The recombinant nucleic acid molecule of claim 1, wherein said pesticidal protein comprises an amino acid sequence having at least 99% identity to the amino acid sequence as set forth in SEQ ID NO:2, SEQ ID NO:4, or SEQ ID NO:10.

29. The recombinant nucleic acid molecule of claim 1, wherein said polynucleotide comprises the nucleotide sequence of SEQ ID NO:1.

30. The recombinant nucleic acid molecule of claim 1, wherein said polynucleotide comprises the nucleotide sequence of SEQ ID NO:3.

31. The recombinant nucleic acid molecule of claim 1, wherein said polynucleotide comprises the nucleotide sequence of SEQ ID NO:5.

32. The recombinant nucleic acid molecule of claim 1, wherein said polynucleotide comprises the nucleotide sequence of SEQ ID NO:6.

33. The recombinant nucleic acid molecule of claim 1, wherein said polynucleotide comprises the nucleotide sequence of SEQ ID NO:7.

34. The recombinant nucleic acid molecule of claim 1, wherein said polynucleotide comprises the nucleotide sequence of SEQ ID NO:8.

35. The recombinant nucleic acid molecule of claim 1, wherein said polynucleotide comprises the nucleotide sequence of SEQ ID NO:9.

* * * * *

SEQUENCE LISTING

```
<160> NUMBER OF SEQ ID NOS: 10

<210> SEQ ID NO 1
<211> LENGTH: 3534
<212> TYPE: DNA
<213> ORGANISM: Bacillus thuringienses
<220> FEATURE:
<221> NAME/KEY: misc_feature
<222> LOCATION: (1)..(3534)
<223> OTHER INFORMATION: Nucleic acid sequence encoding a TIC4029
      pesticidal protein obtained from Bacillus thuringiensis species
      EGBS0016.

<400> SEQUENCE: 1

atgaataata atattgaaaa ccaatgcgta ccttacaatt gtttaagtaa tcctgaagaa      60

gtacttttgg atggagaacg gatatcaact ggtaattcat caattgatat ttctctgtca     120

cttgttcaac ttctggtatc taactttgta ccagggggag gatttttagt tggattaata     180

gattttgtat ggggaatagt aggcccttct caatgggatg catttctagt gcaaattgaa     240

caattaattc agcaaagaat agaagcatat gctagggctg cagcaatttc taatttagaa     300

ggaataggaa acaatttcaa tatatatgtg gaagcatttc aagaatggga agaagatcct     360

aataatccag cgacaagaaa tagagtagtt gatcgctttc gtatacttga tgggctactt     420

gaaagggaca ttccttcgtt tcgaatttct ggatttgaag tcccctttt atccgtttat     480

actcaagcgg ccaatctgca tctagctata ttgagggatt ctgtaatttt tggggaaaga     540

tggggattaa caacgacaaa tgtcaatgaa aactataata gacaaattag gcatattaat     600

gaatatgccg atcactgtgc aaatacgtac aatcggggac tcaataattt accgaaatct     660

acgtatcaag attggataac atataatcga ttacggagag acttaacatt gactgtatta     720

gatatcgtca atttctttcc aaactatgac aataggagat atccaattca aacagttggt     780

caactaacaa gggaagttta tacggaccca ttaattaatt ttaatccaca gttacagtct     840

gtagctcaat tacctacttt taacgttatg gaaagcagcg caattagaaa tcctcattta     900

tttgatgtat tgaataatct tacaattttt acagactggt ttagtgttgg acgcaacttt     960

tattggggag gccatcgagt aatatctagc cgtataggag gtggtaacat aacatctcct    1020
```

-continued

```
atatatggaa gagaggcgaa tcaggagcct ccaagatctt ttacttttaa tggaccggtt   1080
tttaggactc tatcaaatcc tactttaaga tcattacagc aaccttggcc agcgccacca   1140
tttaatttac gtggtgttga aggagtagaa ttttctacac ctacaaatag ctttacgtat   1200
cgaggaagag gtacggttga ttctttaact gagttaccgc ctcaggataa tagtgtgcca   1260
cctcgcgaag gatatagtca tcgtttatgt catgcaactt ttgttcaaag atctggaaca   1320
cctttttttaa caacaggtgt agtattttct tggacgcatc gtagtgccga tcaaaatata   1380
atctatccaa atagaattac ccaaatacca ttggtaaaag catctgatct cccttcaggt   1440
accactgttg ttagaggacc agggtttaca ggtggggata ttcttcgaag aacaagtact   1500
ggtggattcg gcacgataag agtaaatgtt aatggaacac taacacaaag atatcgtata   1560
ggatttcgct atgcttcaac agtagatttt gatttctttg tagtacgtgg agggactact   1620
gtaaataatt ttagattccc acgtacaatg aacagtggag aggaattaag atacggatcc   1680
tttgagacaa ggtctttcac tactcctttt acatttactc aaattcagga tacaattcga   1740
acgtctattc aaggtcttag cggtaatggt gaagtgtatc ttgacagaat cgagatcatt   1800
ccagttactg caaccttaaa ggcagaatat gatttagaaa gagcgcagaa ggtggtgggt   1860
gccctgttta cttccacaaa ccaactagcg ctaaaaacaa atattacgga ttatcatatt   1920
gatcaagttt ccaatttagt ggattgttta tccgatgaat tttgtctgga tgaaaagcga   1980
gaattgtccg agaaagtcaa acatgcgaag cgactcagtg atgagcggaa tttactccaa   2040
gatccaaact ttagaggcat caatagacaa ccagaccgtg gctggagagg aagtacggat   2100
attaccatcc aaggaggaaa tgacgtattc aaagaaaatt acgtcacact accaggtacc   2160
tttgatgagt gttatccaac gtatttgtat caaaaaatag atgaatcaaa attaaaatct   2220
gatacccgtt atcaattaag agggtatatt gaagatagtc aagacttaga aatctattta   2280
attcgctaca atgcaaaaca cgaaacagta aatgttcccg gtacgagttt cttgtggccg   2340
ctttcggtcg aaagtcctat tgggaagtgc ggagaaccga atcgttgcgc accacacatt   2400
gaatggaatc ctgatctaga atgttcctgt agagacggag aaaaatgtgc acatcattcc   2460
catcatttct ccctagacat tgatgttgga tgtacagact taaatgagga cttaggtgta   2520
tgggtgatat tcaagattaa gacgcaagat ggccatgcaa gactagggaa tttagagttt   2580
ctcgaagaga aaccgttatt aggagaagcg ttagctcgtg cgaaaagagc ggagaaaaaa   2640
tggagagaca aacgcgaaac attgcaattg gaaacaaata ttgtttataa agaggcaaaa   2700
gaatctgtag atgctttatt tgtgaactct caatatgata gattacaagc ggataccgac   2760
atcgcgatga ttcatgcggc agataaacgc gttcatcgaa ttcgagaagc atatcttcca   2820
gagttatctg taattccggg tgtaaatgcg ggtatttttg aagaattaga gggacgtatt   2880
ttcacagcat actctctata tgatgcgaga aatgtcatta aaaatggcga tttcaataat   2940
ggcttatcat gctggaacgt gaaagggcat gtagatatag aagaacaaaa caaccaccgt   3000
tcggttcttg ttgtcccgga atgggaagca gaagtgtcac aagaagttcg tgtctgtcca   3060
ggacgtggtt atatccttcg agtcacagcg tacaaagagg gatatggaga aggttgtgta   3120
accattcatg aaattgaaga tcatacagat gaactaaagt ttagcaactg tgtagaagag   3180
gacgcatatc caggtaatac ggtggcatgt gataattatc ccgcgaatca agaagaagga   3240
tgtacagagt tacgtcattc cggtaatcgc ggatatgatg aaacctatgt gaattctact   3300
tcctcatcca ctgattacac agcggtctat aaggaagaat catatacggg tgaacagaga   3360
```

tatgattctt gtgaatctaa cagaggatat gggaattata cgccactacc agctggttat 3420
gtgacaaaag agttagagta cttcccagaa accgataagg tatggattga gatcggagaa 3480
acggaaggaa cattcatcgt agacagcgtg gaattactcc ttatggaaga atag 3534

<210> SEQ ID NO 2
<211> LENGTH: 1177
<212> TYPE: PRT
<213> ORGANISM: Bacillus thuringienses
<220> FEATURE:
<221> NAME/KEY: MISC_FEATURE
<222> LOCATION: (1)..(1177)
<223> OTHER INFORMATION: Amino acid sequence of the TIC4029 pesticidal protein.

<400> SEQUENCE: 2

Met Asn Asn Asn Ile Glu Asn Gln Cys Val Pro Tyr Asn Cys Leu Ser
1 5 10 15

Asn Pro Glu Glu Val Leu Leu Asp Gly Glu Arg Ile Ser Thr Gly Asn
20 25 30

Ser Ser Ile Asp Ile Ser Leu Ser Leu Val Gln Leu Leu Val Ser Asn
35 40 45

Phe Val Pro Gly Gly Gly Phe Leu Val Gly Leu Ile Asp Phe Val Trp
50 55 60

Gly Ile Val Gly Pro Ser Gln Trp Asp Ala Phe Leu Val Gln Ile Glu
65 70 75 80

Gln Leu Ile Gln Gln Arg Ile Glu Ala Tyr Ala Arg Ala Ala Ala Ile
85 90 95

Ser Asn Leu Glu Gly Ile Gly Asn Asn Phe Asn Ile Tyr Val Glu Ala
100 105 110

Phe Gln Glu Trp Glu Glu Asp Pro Asn Asn Pro Ala Thr Arg Asn Arg
115 120 125

Val Val Asp Arg Phe Arg Ile Leu Asp Gly Leu Leu Glu Arg Asp Ile
130 135 140

Pro Ser Phe Arg Ile Ser Gly Phe Glu Val Pro Leu Leu Ser Val Tyr
145 150 155 160

Thr Gln Ala Ala Asn Leu His Leu Ala Ile Leu Arg Asp Ser Val Ile
165 170 175

Phe Gly Glu Arg Trp Gly Leu Thr Thr Thr Asn Val Asn Glu Asn Tyr
180 185 190

Asn Arg Gln Ile Arg His Ile Asn Glu Tyr Ala Asp His Cys Ala Asn
195 200 205

Thr Tyr Asn Arg Gly Leu Asn Asn Leu Pro Lys Ser Thr Tyr Gln Asp
210 215 220

Trp Ile Thr Tyr Asn Arg Leu Arg Arg Asp Leu Thr Leu Thr Val Leu
225 230 235 240

Asp Ile Val Asn Phe Phe Pro Asn Tyr Asp Asn Arg Arg Tyr Pro Ile
245 250 255

Gln Thr Val Gly Gln Leu Thr Arg Glu Val Tyr Thr Asp Pro Leu Ile
260 265 270

Asn Phe Asn Pro Gln Leu Gln Ser Val Ala Gln Leu Pro Thr Phe Asn
275 280 285

Val Met Glu Ser Ser Ala Ile Arg Asn Pro His Leu Phe Asp Val Leu
290 295 300

Asn Asn Leu Thr Ile Phe Thr Asp Trp Phe Ser Val Gly Arg Asn Phe
305 310 315 320

-continued

```
Tyr Trp Gly Gly His Arg Val Ile Ser Ser Arg Ile Gly Gly Gly Asn
                325                 330                 335

Ile Thr Ser Pro Ile Tyr Gly Arg Glu Ala Asn Gln Glu Pro Pro Arg
            340                 345                 350

Ser Phe Thr Phe Asn Gly Pro Val Phe Arg Thr Leu Ser Asn Pro Thr
        355                 360                 365

Leu Arg Ser Leu Gln Gln Pro Trp Pro Ala Pro Pro Phe Asn Leu Arg
    370                 375                 380

Gly Val Glu Gly Val Glu Phe Ser Thr Pro Thr Asn Ser Phe Thr Tyr
385                 390                 395                 400

Arg Gly Arg Gly Thr Val Asp Ser Leu Thr Glu Leu Pro Pro Gln Asp
                405                 410                 415

Asn Ser Val Pro Pro Arg Glu Gly Tyr Ser His Arg Leu Cys His Ala
            420                 425                 430

Thr Phe Val Gln Arg Ser Gly Thr Pro Phe Leu Thr Thr Gly Val Val
        435                 440                 445

Phe Ser Trp Thr His Arg Ser Ala Asp Gln Asn Ile Ile Tyr Pro Asn
    450                 455                 460

Arg Ile Thr Gln Ile Pro Leu Val Lys Ala Ser Asp Leu Pro Ser Gly
465                 470                 475                 480

Thr Thr Val Val Arg Gly Pro Gly Phe Thr Gly Gly Asp Ile Leu Arg
                485                 490                 495

Arg Thr Ser Thr Gly Gly Phe Gly Thr Ile Arg Val Asn Val Asn Gly
            500                 505                 510

Thr Leu Thr Gln Arg Tyr Arg Ile Gly Phe Arg Tyr Ala Ser Thr Val
        515                 520                 525

Asp Phe Asp Phe Phe Val Val Arg Gly Gly Thr Thr Val Asn Asn Phe
    530                 535                 540

Arg Phe Pro Arg Thr Met Asn Ser Gly Glu Glu Leu Arg Tyr Gly Ser
545                 550                 555                 560

Phe Glu Thr Arg Ser Phe Thr Thr Pro Phe Thr Phe Thr Gln Ile Gln
                565                 570                 575

Asp Thr Ile Arg Thr Ser Ile Gln Gly Leu Ser Gly Asn Gly Glu Val
            580                 585                 590

Tyr Leu Asp Arg Ile Glu Ile Ile Pro Val Thr Ala Thr Leu Lys Ala
        595                 600                 605

Glu Tyr Asp Leu Glu Arg Ala Gln Lys Val Val Gly Ala Leu Phe Thr
    610                 615                 620

Ser Thr Asn Gln Leu Ala Leu Lys Thr Asn Ile Thr Asp Tyr His Ile
625                 630                 635                 640

Asp Gln Val Ser Asn Leu Val Asp Cys Leu Ser Asp Glu Phe Cys Leu
                645                 650                 655

Asp Glu Lys Arg Glu Leu Ser Glu Lys Val Lys His Ala Lys Arg Leu
            660                 665                 670

Ser Asp Glu Arg Asn Leu Leu Gln Asp Pro Asn Phe Arg Gly Ile Asn
        675                 680                 685

Arg Gln Pro Asp Arg Gly Trp Arg Gly Ser Thr Asp Ile Thr Ile Gln
    690                 695                 700

Gly Gly Asn Asp Val Phe Lys Glu Asn Tyr Val Thr Leu Pro Gly Thr
705                 710                 715                 720

Phe Asp Glu Cys Tyr Pro Thr Tyr Leu Tyr Gln Lys Ile Asp Glu Ser
                725                 730                 735

Lys Leu Lys Ser Asp Thr Arg Tyr Gln Leu Arg Gly Tyr Ile Glu Asp
```

-continued

```
            740                 745                 750

Ser Gln Asp Leu Glu Ile Tyr Leu Ile Arg Tyr Asn Ala Lys His Glu
        755                 760                 765

Thr Val Asn Val Pro Gly Thr Ser Phe Leu Trp Pro Leu Ser Val Glu
    770                 775                 780

Ser Pro Ile Gly Lys Cys Gly Glu Pro Asn Arg Cys Ala Pro His Ile
785                 790                 795                 800

Glu Trp Asn Pro Asp Leu Glu Cys Ser Cys Arg Asp Gly Glu Lys Cys
                805                 810                 815

Ala His His Ser His His Phe Ser Leu Asp Ile Asp Val Gly Cys Thr
            820                 825                 830

Asp Leu Asn Glu Asp Leu Gly Val Trp Val Ile Phe Lys Ile Lys Thr
        835                 840                 845

Gln Asp Gly His Ala Arg Leu Gly Asn Leu Glu Phe Leu Glu Glu Lys
    850                 855                 860

Pro Leu Leu Gly Glu Ala Leu Ala Arg Ala Lys Arg Ala Glu Lys Lys
865                 870                 875                 880

Trp Arg Asp Lys Arg Glu Thr Leu Gln Leu Glu Thr Asn Ile Val Tyr
                885                 890                 895

Lys Glu Ala Lys Glu Ser Val Asp Ala Leu Phe Val Asn Ser Gln Tyr
            900                 905                 910

Asp Arg Leu Gln Ala Asp Thr Asp Ile Ala Met Ile His Ala Ala Asp
        915                 920                 925

Lys Arg Val His Arg Ile Arg Glu Ala Tyr Leu Pro Glu Leu Ser Val
    930                 935                 940

Ile Pro Gly Val Asn Ala Gly Ile Phe Glu Glu Leu Glu Gly Arg Ile
945                 950                 955                 960

Phe Thr Ala Tyr Ser Leu Tyr Asp Ala Arg Asn Val Ile Lys Asn Gly
                965                 970                 975

Asp Phe Asn Asn Gly Leu Ser Cys Trp Asn Val Lys Gly His Val Asp
            980                 985                 990

Ile Glu Glu Gln Asn Asn His Arg  Ser Val Leu Val Val  Pro Glu Trp
        995                 1000                1005

Glu Ala  Glu Val Ser Gln Glu  Val Arg Val Cys Pro  Gly Arg Gly
    1010                1015                1020

Tyr Ile  Leu Arg Val Thr Ala  Tyr Lys Glu Gly Tyr  Gly Glu Gly
    1025                1030                1035

Cys Val  Thr Ile His Glu Ile  Glu Asp His Thr Asp  Glu Leu Lys
    1040                1045                1050

Phe Ser  Asn Cys Val Glu Glu  Asp Ala Tyr Pro Gly  Asn Thr Val
    1055                1060                1065

Ala Cys  Asp Asn Tyr Pro Ala  Asn Gln Glu Glu Gly  Cys Thr Glu
    1070                1075                1080

Leu Arg  His Ser Gly Asn Arg  Gly Tyr Asp Glu Thr  Tyr Val Asn
    1085                1090                1095

Ser Thr  Ser Ser Ser Thr Asp  Tyr Thr Ala Val Tyr  Lys Glu Glu
    1100                1105                1110

Ser Tyr  Thr Gly Glu Gln Arg  Tyr Asp Ser Cys Glu  Ser Asn Arg
    1115                1120                1125

Gly Tyr  Gly Asn Tyr Thr Pro  Leu Pro Ala Gly Tyr  Val Thr Lys
    1130                1135                1140

Glu Leu  Glu Tyr Phe Pro Glu  Thr Asp Lys Val Trp  Ile Glu Ile
    1145                1150                1155
```

-continued

```
Gly Glu  Thr Glu Gly Thr Phe  Ile Val Asp Ser Val  Glu Leu Leu
    1160                 1165                 1170

Leu Met  Glu Glu
    1175

<210> SEQ ID NO 3
<211> LENGTH: 1812
<212> TYPE: DNA
<213> ORGANISM: Artificial
<220> FEATURE:
<223> OTHER INFORMATION: Nucleic acid sequence encoding a TIC4029_1
      pesticidal protein comprising a truncation wherein the coding
      sequence encoding the protoxin domain of TIC4029 has been deleted.

<400> SEQUENCE: 3
atgaataata atattgaaaa ccaatgcgta ccttacaatt gtttaagtaa tcctgaagaa     60
gtacttttgg atggagaacg gatatcaact ggtaattcat caattgatat ttctctgtca    120
cttgttcaac ttctggtatc taactttgta ccagggggag gatttttagt tggattaata    180
gattttgtat ggggaatagt aggcccttct caatgggatg catttctagt gcaaattgaa    240
caattaattc agcaaagaat agaagcatat gctagggctg cagcaatttc taatttagaa    300
ggaataggaa acaatttcaa tatatatgtg gaagcatttc aagaatggga agaagatcct    360
aataatccag cgacaagaaa tagagtagtt gatcgctttc gtatacttga tgggctactt    420
gaaagggaca ttccttcgtt tcgaatttct ggatttgaag tccccctttt atccgtttat    480
actcaagcgg ccaatctgca tctagctata ttgagggatt ctgtaatttt tggggaaaga    540
tggggattaa caacgacaaa tgtcaatgaa aactataata gacaaattag gcatattaat    600
gaatatgccg atcactgtgc aaatacgtac aatcggggac tcaataattt accgaaatct    660
acgtatcaag attggataac atataatcga ttacggagag acttaacatt gactgtatta    720
gatatcgtca atttctttcc aaactatgac aataggagat atccaattca aacagttggt    780
caactaacaa gggaagttta tacggaccca ttaattaatt ttaatccaca gttacagtct    840
gtagctcaat tacctacttt taacgttatg gaaagcagcg caattagaaa tcctcattta    900
tttgatgtat tgaataatct tacaattttt acagactggt ttagtgttgg acgcaacttt    960
tattggggag gccatcgagt aatatctagc cgtataggag gtggtaacat aacatctcct   1020
atatatggaa gagaggcgaa tcaggagcct ccaagatctt ttacttttaa tggaccggtt   1080
tttaggactc tatcaaatcc tactttaaga tcattacagc aaccttggcc agcgccacca   1140
tttaatttac gtggtgttga aggagtagaa ttttctacac ctacaaatag ctttacgtat   1200
cgaggaagag gtacggttga ttctttaact gagttaccgc ctcaggataa tagtgtgcca   1260
cctcgcgaag gatatagtca tcgtttatgt catgcaactt ttgttcaaag atctggaaca   1320 cctttttaa caacaggtgt agtattttct tggacgcatc gtagtgccga tcaaaatata   1380
atctatccaa atagaattac ccaaatacca ttggtaaaag catctgatct cccttcaggt   1440
accactgttg ttagaggacc agggtttaca ggtggggata ttcttcgaag aacaagtact   1500
ggtggattcg gcacgataag agtaaatgtt aatggaacac taacacaaag atatcgtata   1560
ggatttcgct atgcttcaac agtagatttt gatttctttg tagtacgtgg agggactact   1620
gtaaataatt ttagattccc acgtacaatg aacagtggag aggaattaag atacggatcc   1680
tttgagacaa ggtctttcac tactcctttt acatttactc aaattcagga tacaattcga   1740
acgtctattc aaggtcttag cggtaatggt gaagtgtatc ttgacagaat cgagatcatt   1800
```

-continued ccagttactt ag 1812

<210> SEQ ID NO 4
<211> LENGTH: 603
<212> TYPE: PRT
<213> ORGANISM: Artificial
<220> FEATURE:
<223> OTHER INFORMATION: Amino acid sequence of the TIC4029_1 pesticidal protein comprising a truncation of the protoxin domain.

<400> SEQUENCE: 4

Met Asn Asn Asn Ile Glu Asn Gln Cys Val Pro Tyr Asn Cys Leu Ser
1 5 10 15

Asn Pro Glu Glu Val Leu Leu Asp Gly Glu Arg Ile Ser Thr Gly Asn
20 25 30

Ser Ser Ile Asp Ile Ser Leu Ser Leu Val Gln Leu Leu Val Ser Asn
35 40 45

Phe Val Pro Gly Gly Gly Phe Leu Val Gly Leu Ile Asp Phe Val Trp
50 55 60

Gly Ile Val Gly Pro Ser Gln Trp Asp Ala Phe Leu Val Gln Ile Glu
65 70 75 80

Gln Leu Ile Gln Gln Arg Ile Glu Ala Tyr Ala Arg Ala Ala Ala Ile
85 90 95

Ser Asn Leu Glu Gly Ile Gly Asn Asn Phe Asn Ile Tyr Val Glu Ala
100 105 110

Phe Gln Glu Trp Glu Glu Asp Pro Asn Asn Pro Ala Thr Arg Asn Arg
115 120 125

Val Val Asp Arg Phe Arg Ile Leu Asp Gly Leu Leu Glu Arg Asp Ile
130 135 140

Pro Ser Phe Arg Ile Ser Gly Phe Glu Val Pro Leu Leu Ser Val Tyr
145 150 155 160

Thr Gln Ala Ala Asn Leu His Leu Ala Ile Leu Arg Asp Ser Val Ile
165 170 175

Phe Gly Glu Arg Trp Gly Leu Thr Thr Thr Asn Val Asn Glu Asn Tyr
180 185 190

Asn Arg Gln Ile Arg His Ile Asn Glu Tyr Ala Asp His Cys Ala Asn
195 200 205

Thr Tyr Asn Arg Gly Leu Asn Asn Leu Pro Lys Ser Thr Tyr Gln Asp
210 215 220

Trp Ile Thr Tyr Asn Arg Leu Arg Arg Asp Leu Thr Leu Thr Val Leu
225 230 235 240

Asp Ile Val Asn Phe Phe Pro Asn Tyr Asp Asn Arg Arg Tyr Pro Ile
245 250 255

Gln Thr Val Gly Gln Leu Thr Arg Glu Val Tyr Thr Asp Pro Leu Ile
260 265 270

Asn Phe Asn Pro Gln Leu Gln Ser Val Ala Gln Leu Pro Thr Phe Asn
275 280 285

Val Met Glu Ser Ser Ala Ile Arg Asn Pro His Leu Phe Asp Val Leu
290 295 300

Asn Asn Leu Thr Ile Phe Thr Asp Trp Phe Ser Val Gly Arg Asn Phe
305 310 315 320

Tyr Trp Gly Gly His Arg Val Ile Ser Ser Arg Ile Gly Gly Gly Asn
325 330 335

Ile Thr Ser Pro Ile Tyr Gly Arg Glu Ala Asn Gln Glu Pro Pro Arg
340 345 350

-continued

```
Ser Phe Thr Phe Asn Gly Pro Val Phe Arg Thr Leu Ser Asn Pro Thr
        355                 360                 365

Leu Arg Ser Leu Gln Gln Pro Trp Pro Ala Pro Pro Phe Asn Leu Arg
    370                 375                 380

Gly Val Glu Gly Val Glu Phe Ser Thr Pro Thr Asn Ser Phe Thr Tyr
385                 390                 395                 400

Arg Gly Arg Gly Thr Val Asp Ser Leu Thr Glu Leu Pro Pro Gln Asp
                405                 410                 415

Asn Ser Val Pro Pro Arg Glu Gly Tyr Ser His Arg Leu Cys His Ala
            420                 425                 430

Thr Phe Val Gln Arg Ser Gly Thr Pro Phe Leu Thr Thr Gly Val Val
        435                 440                 445

Phe Ser Trp Thr His Arg Ser Ala Asp Gln Asn Ile Ile Tyr Pro Asn
    450                 455                 460

Arg Ile Thr Gln Ile Pro Leu Val Lys Ala Ser Asp Leu Pro Ser Gly
465                 470                 475                 480

Thr Thr Val Val Arg Gly Pro Gly Phe Thr Gly Gly Asp Ile Leu Arg
                485                 490                 495

Arg Thr Ser Thr Gly Gly Phe Gly Thr Ile Arg Val Asn Val Asn Gly
            500                 505                 510

Thr Leu Thr Gln Arg Tyr Arg Ile Gly Phe Arg Tyr Ala Ser Thr Val
        515                 520                 525

Asp Phe Asp Phe Phe Val Val Arg Gly Gly Thr Thr Val Asn Asn Phe
    530                 535                 540

Arg Phe Pro Arg Thr Met Asn Ser Gly Glu Glu Leu Arg Tyr Gly Ser
545                 550                 555                 560

Phe Glu Thr Arg Ser Phe Thr Thr Pro Phe Thr Phe Thr Gln Ile Gln
                565                 570                 575

Asp Thr Ile Arg Thr Ser Ile Gln Gly Leu Ser Gly Asn Gly Glu Val
            580                 585                 590

Tyr Leu Asp Arg Ile Glu Ile Ile Pro Val Thr
        595                 600
```

```
<210> SEQ ID NO 5
<211> LENGTH: 3534
<212> TYPE: DNA
<213> ORGANISM: Artificial
<220> FEATURE:
<223> OTHER INFORMATION: Synthetic coding sequence used for expression
      in a plant cell, TIC4029PL-1 encoding TIC4029.

<400> SEQUENCE: 5

atgaacaaca acattgagaa ccagtgcgtg ccctacaact gcctgagcaa ccctgaggag      60

gtgctcctag acggtgagcg catctccacc ggtaactcta gcatcgacat ctccctgagc     120

ctagtgcagc tcctagtgtc taacttcgtg cccggcggtg gcttcctcgt gggcctcatc     180

gacttcgtgt ggggcatcgt gggcccctcc cagtgggacg ccttcctcgt gcagatcgag     240

cagctcatcc agcaacgcat cgaggcctac gcccgcgccg ctgccatcag caacctcgag     300

ggcatcggca acaatttcaa catctacgtg gaggccttcc aggagtggga ggaagacccc     360

aacaatcccg ccacccgcaa ccgcgtggtc gaccgcttcc gcatcctcga cggcctcctg     420

gagcgcgaca tcccctcctt ccgcatctcc ggcttcgagg tgcccctcct gtccgtgtac     480

acccaggccg ctaacctcca cctcgccatc ctccgcgact ccgtgatctt cggcgagcgc     540

tggggcctca ccactaccaa cgtgaacgag aactacaacc gccagatccg ccacatcaac     600
```

-continued

```
gagtacgccg accactgcgc caacacctac aaccgcggcc tcaacaatct ccccaagtcc    660
acctaccagg actggatcac ctacaaccgc ctccgcaggg acctcaccct caccgtgctc    720
gacatcgtga acttctttcc caactacgac aaccgcaggt accccatcca gaccgtgggc    780
cagctcaccc gcgaggtgta caccgacccc ctcatcaact tcaacccccca gctccagtcc    840
gtggcccagc tccccacctt caacgtgatg gagtccagcg ccatccgcaa cccccacctc    900
ttcgacgtgc tcaacaatct caccatcttc accgactggt tctccgtggg ccgcaacttc    960
tactggggcg gtcaccgcgt gatctccagc cgcatcggcg gtggcaacat cacctccccc   1020
atctacggcc gcgaggccaa ccaggagcct ccgcgctcct tcaccttcaa cggccctgtg   1080
ttccgcaccc tctccaaccc taccctcagg tccctccagc aaccttggcc tgcccctccg   1140
ttcaacctca ggggcgtgga gggcgtggag ttctccaccc ctaccaactc cttcacctac   1200
aggggcaggg gcaccgtgga ctccctcacc gagctgcctc cgcaggacaa ctccgtgcct   1260
ccgagggagg gctacagcca caggctgtgc cacgccacct tcgtgcagag gagcggcacc   1320
cctttcctga ccactggcgt cgttttcagc tggacccaca ggagcgccga ccagaacatc   1380
atttacccta acaggatcac ccagatccct ctggtcaagg ccagcgacct gcctagcggc   1440
accactgtcg ttaggggccc tggcttcacc ggcggtgaca tcctgaggcg gaccagcacc   1500
ggcggtttcg gcaccatcag ggtcaacgtc aacggcaccc tgactcagag gtacaggatc   1560
ggcttcaggt acgccagcac tgtcgacttc gacttctttg tcgttagggg cggtactact   1620
gtcaacaatt tcaggttccc gaggactatg aacagcggcg aggaactgag gtacggtagc   1680
ttcgagacta ggtctttcac tacgccgttc actttcactc agatccagga cactatccgg   1740
actagtatcc agggtctgtc tggtaacggt gaggtctacc tggaccggat cgagatcatt   1800
ccggtcactg ctactctgaa ggctgagtac gacctggagc gggctcagaa ggtcgttggt   1860
gctctgttca cttctactaa ccagctggct ctgaagacta acatcactga ctaccacatc   1920
gaccaggtct ctaacctggt cgactgcctg tctgacgagt tctgcctgga cgagaagcgg   1980
gagctgtctg agaaggtcaa gcacgctaag cggctgtctg acgagcggaa cctgcttcag   2040
gacccgaact tccggggtat caaccggcag ccggaccggg gttggcgggg tagtactgac   2100
atcactattc agggtgggaa cgacgtcttt aaggagaact acgtcacgct gccgggtacg   2160
tttgacgagt gctacccgac gtacctgtac cagaagattg acgagtctaa gctgaagtct   2220
gacacgcgtt accagctgcg tggttacatt gaggatagtc aggatcttga gatttacctt   2280
attcgttaca acgctaagca cgagacggtc aacgtcccgg gtacgtcttt tctttggccg   2340
ctttctgtcg agtcgccgat tgggaagtgc ggggagccaa accgttgcgc tccacacatt   2400
gagtggaacc cagatcttga gtgctcgtgc cgtgatgggg agaagtgcgc tcaccatagt   2460
caccatttta gtcttgatat tgatgtcggg tgcacggatc ttaatgagga tcttggggtc   2520
tgggtcattt ttaagattaa gacgcaagat gggcacgcta gacttgggaa tcttgagttt   2580
cttgaggaaa agccactttt gggggaggct cttgctagag ctaagcgtgc ggagaagaaa   2640
tggcgtgata agcgtgagac gcttcaactt gagacgaata ttgtctacaa ggaggcgaag   2700
gagtcggtcg atgcgctttt tgtcaatagt caatacgata gacttcaagc ggatacggat   2760
attgcgatga ttcacgcggc agataagcgt gtccatagaa ttcgtgaggc gtaccttcca   2820
gagttgtcgg tcattccagg ggttaatgcg gggatttttg aggaattgga ggggcgtatt   2880
tttacggcgt actcgttgta cgatgcgaga aatgttatta agaatgggga ttttaataat   2940
gggttgtcgt gctggaatgt taaggggcat gttgatatag aggaacaaaa taatcataga   3000
```

```
tcggttttgg ttgtaccaga gtgggaggca gaggtttcgc aagaggttag agtttgccca   3060

gggagaggat acatattgag agttacggca tataaggagg gatatggaga gggatgtgtt   3120

acgatacatg agatagagga tcatacagat gagttgaaat ttagtaattg tgttgaggaa   3180

gatgcatatc caggaaatac agttgcatgt gataattatc cagcaaatca agaggaagga   3240

tgtacagagt tgcgacattc gggaaatcga ggatatgatg aaacatatgt taattcaaca   3300

tcatcatcaa cagattatac agcagtttat aaagaagaat catatacagg agaacaacga   3360

tatgattcat gtgaatcaaa tcgaggatat ggaaattata caccactacc agcaggatat   3420

gttacaaaag aactagaata ttttccagaa acagataaag tatggataga aataggagaa   3480

acagaaggaa catttatagt agattcagta gaattattat tgatggaaga atga         3534
```

```
<210> SEQ ID NO 6
<211> LENGTH: 3534
<212> TYPE: DNA
<213> ORGANISM: Artificial
<220> FEATURE:
<223> OTHER INFORMATION: Synthetic coding sequence used for expression
      in a plant cell, TIC4029PL-2 encoding TIC4029.

<400> SEQUENCE: 6
```

```
atgaacaaca acatcgagaa ccagtgcgtc ccctacaact gcctgtcgaa cccagaggag     60

gtgctgctag acggcgagcg tatctcaacg ggcaacagct ccatcgacat ctccctttcg    120

ctcgtgcagc tcttggtgtc caacttcgtg cccggcggtg gattcctggt ggggctgatc    180

gacttcgtgt ggggcattgt cggccctagc cagtgggatg ctttcctcgt tcagatcgaa    240

caactgatac agcagcggat cgaagcctac gcccgcgccg ccgcgattag caacttagag    300

gggatcggca acaacttcaa catctatgtg gaggcgttcc aggagtggga ggaagaccca    360

aacaaccccg cgacccgcaa tcgcgtagtt gatcgtttcc gcatcctgga cggccttctg    420

gagcgagaca ttccttcgtt tcgcatcagc gggttcgaag tgccgctgct ttcagtctat    480

acccaggcgg cgaacctgca ccttgcaatc ctcagggact cggtgatctt cggcgagcgt    540

tggggcttga cgactacgaa cgtcaatgag aattacaata gacagatccg ccacatcaac    600

gagtacgccg accactgcgc gaacacctac aaccgtgggc ttaacaacct ccctaagagc    660

acgtaccaag actggataac atacaaccgg ctccgtcgtg acctcacact tacggtcttg    720

gacattgtga acttcttccc caactacgac aaccgccgtt acccgatcca gacggtcggc    780

cagctcactc gggaggtcta taccgacccg ctcatcaact tcaacccgca gttgcagagc    840

gtcgcccagc tccccacgtt taacgtgatg gaaagctcgg ccatacggaa cccgcaccta    900

ttcgacgtgc tgaacaacct cacgatcttc accgactggt tcagtgtcgg gcgcaacttc    960

tactggggcg gacaccgcgt tatctccagc cggatcggcg gaggcaacat taccagcccg   1020

atctacggcc gcgaggccaa ccaggagcca ccgcgctcgt tcactttcaa cggccccgtc   1080

tttcggaccc ttagcaatcc aacactgcgt tcactccaac aaccctggcc tgcgccacct   1140

ttcaacctca gaggcgttga gggtgttgag ttctcaaccc cgacaaattc gttcacctat   1200

cgcgggcgcg gaaccgtgga cagtctcacc gagctgccgc cacaggacaa tagtgttcct   1260

ccacgggagg gatattccca ccgcttgtgc catgcgacct tcgtgcagag gtccgggaca   1320

ccgttcctga ccaccggcgt cgtattctcg tggacccacc gctctgctga ccagaacatt   1380

atctacccga accgtatcac gcagatacca ctggttaagg cttccgacct cccctccggg   1440

acaaccgtcg tgcgcgggcc cggattcaca ggcggcgaca tccttcggcg cacctcgacg   1500
```

ggtggcttcg gcaccatcag ggtcaacgtg aacggcactc tgacgcagcg ctatcgcatc 1560
ggtttccgtt acgcctcgac ggtggacttc gatttctttg tcgtgcgtgg cggaaccacg 1620
gtcaacaatt tccgtttccc acgcaccatg aactctggtg aggaactgcg ttacggcagc 1680
ttcgaaactc ggtccttcac aaccccattc accttcaccc aaatccagga caccatccga 1740
accagtatcc agggcttgag cgggaacggc gaagtgtacc tggaccgcat cgagatcatc 1800
ccggtgactg cgaccttgaa agcggagtac gacctggagc gggcgcagaa ggtggtgggt 1860
gcgctgttca cctccacaaa tcagctcgca ttgaaaacga acatcactga ctaccatatc 1920
gaccaagtga gcaaccttgt ggactgcctg agcgacgagt tctgtcttga cgagaaacgt 1980
gagctgtccg aaaaggttaa gcacgccaag aggctgagcg acgagcgcaa tctcctgcaa 2040
gacccgaact ttcgagggat caaccggcag ccggatcgag gctggcgtgg ctccacggac 2100
attaccatcc agggaggcaa cgacgtcttc aaggagaact acgtcaccct gccggggacg 2160
ttcgacgagt gctatccaac gtacctctat cagaaaatcg acgagagcaa actcaagagt 2220
gacacacgct accagctcag agggtacatc gaggacagcc aagacttaga gatctatctt 2280
attcggtaca acgccaagca cgagaccgtg aacgttcccg gtacgtcctt cctctggccg 2340
ctgagtgtgg agagccccat cgggaagtgc ggagagccaa accgttgcgc tccccacatc 2400
gagtggaacc ctgacctgga atgctcgtgc cgggacgggg agaagtgcgc gcatcattct 2460
caccactttt cccttgatat tgacgtcggg tgcaccgacc tcaacgagga tctgggcgta 2520
tgggtgatat tcaagattaa gacccaggac ggccatgctc ggctcgggaa cctagagttc 2580
ctggaggaga agccgttact gggcgaggcc ctggccagag ccaagcgcgc ggagaagaag 2640
tggcgtgaca agcgggagac cttacagctt gagaccaaca tcgtgtacaa ggaggcaaag 2700
gaaagcgttg acgcactctt cgtgaactct cagtacgaca gactacaggc cgacaccgac 2760
atcgccatga ttcacgctgc cgacaagcgg gtgcacagaa tacgggaagc ctatctgccc 2820
gagctgagtg tgatccctgg ggtgaacgct ggcatcttcg aggagctgga gggccgaatc 2880
ttcaccgcgt actccctcta cgacgcaagg aacgtcatca agaacggcga tttcaacaac 2940
ggccttagct gctggaacgt gaagggtcac gtggatattg aggagcagaa caaccatcgc 3000
tcggtgctcg tggtgccgga gtgggaggcg gaggtgagcc aggaggtccg ggtgtgccca 3060
gggcgcgggt atatccttcg ggtgacggcc tacaaggagg gatacggcga ggggtgcgtg 3120
acgatccatg agattgaaga ccacaccgac gagttaaagt tcagtaattg cgtcgaggag 3180
gatgcgtacc ctgggaacac ggtggcttgc gacaactacc cggcaaacca ggaggagggg 3240
tgcacagagc tgcgccacag cgggaaccgg ggctacgacg agacttatgt caactctact 3300
agcagctcga cggactacac cgctgtgtac aaggaggagt cctacactgg cgagcagcgc 3360
tacgacagtt gcgagtcgaa ccggggttac gggaattaca cgccgctccc ggcgggctac 3420
gtcactaagg agctggagta tttcccagag accgataagg tctggataga gatcggcgag 3480
acagagggca cgttcattgt cgattcggtg gagctgctcc tgatggagga gtga 3534

<210> SEQ ID NO 7
<211> LENGTH: 3534
<212> TYPE: DNA
<213> ORGANISM: Artificial
<220> FEATURE:
<223> OTHER INFORMATION: Synthetic coding sequence used for expression in a plant cell, TIC4029PL-3 encoding TIC4029.

<400> SEQUENCE: 7

-continued

```
atgaacaaca acatcgagaa tcagtgcgtg ccctacaact gcctaagcaa ccctgaggag     60
gtgctcctag acggcgaacg catctccacc gggaactcta gcatcgacat ctctctgagc    120
ctagtgcaac tcctagtgtc gaacttcgtg cctggcggtg gcttcctcgt tggcttgatc    180
gacttcgtgt ggggtatcgt gggcccctcc cagtgggacg ccttcctcgt tcaaatcgag    240
cagctcatac aacaacgcat cgaggcttac gcccgcgccg ctgccatcag taacctagag    300
ggcatcggca acaacttcaa catctacgtg gaagccttcc aagagtggga ggaagaccca    360
aacaaccccg ccacccgcaa ccgcgtggtg gaccgctttc gaatcctcga cggcctcctg    420
gagcgcgaca tcccctcctt ccggatctcc ggtttcgagg tgcccctcct gtccgtttac    480
acccaggccg ctaacttgca cctcgccatc ctccgcgact ccgtgatctt cggggagcgc    540
tggggcctca ccactaccaa cgtgaacgag aactacaacc gtcagatccg ccacatcaac    600
gagtacgccg accactgcgc caacacctac aatcgcggcc tcaacaatct ccccaagtcc    660
acctaccaag actggatcac ctacaaccgc ttgagaaggg atctcactct caccgtgctc    720
gacatcgtga acttctttcc caactatgat aaccgtcgtt atcccattca aaccgtgggc    780
cagctcaccc gcgaagtcta taccgaccca ctcattaact tcaaccctca gctccaatcc    840
gttgcccagc tccccacctt caacgtgatg gagtcctcgg caatccgcaa ccctcactta    900
ttcgacgtgc ttaacaattt gaccatcttc accgactggt tctccgtggg ccgcaacttc    960
tactggggcg gtcaccgcgt gatctctagc cgcatcggag gtggcaacat cacctcccca   1020
atctacggcc gcgaggctaa tcaggagcct ccgcgttcct ttaccttcaa cggccctgtg   1080
ttccgcaccc tttccaaccc taccottaga tcactccaac aaccctggcc cgcaccaccg   1140
ttcaacttac gcggcgtgga gggcgttgag ttctccaccc ctaccaactc ctttacctat   1200
cgcggtagag gcaccgtgga ttccctcact gaactgcctc cgcaagacaa ttccgtgcct   1260
ccgagggagg gctactctca ccgtctgtgc catgccacct tcgtgcaaag gagcggcacc   1320
cctttcctga ccactggcgt cgtgttctcc tggacccacc gatcagccga ccaaaacatc   1380
atatacccaa accgcatcac ccagatccct ctggtcaagg ccagcgacct gcctagcggc   1440
accactgtcg ttcgaggccc tgggttcacc ggcggtgaca tcctgaggcg gaccagcacc   1500
ggcggtttcg gcaccataag ggtcaacgtc aacggcaccc tgactcaaag ataccgtatc   1560
ggctttcgtt acgccagcac agtcgatttc gacttcttcg tcgtaagggg cggaactact   1620
gtcaacaatt tccgcttccc gcgtactatg aactctggcg aggaactgag atacgggagt   1680
ttcgagacaa ggagcttcac tacgccgttt actttcactc aaattcaaga cactatccgg   1740
accagcatac aaggtttaag tggaaacgga gaagtctatc tggaccggat cgagatcatt   1800
cctgtcactg ctactctaaa agctgagtac gacctggagc gggctcagaa ggtcgttggt   1860
gctctgttca cttctactaa ccagttggct ctgaaaacaa acatcactga ttaccacatt   1920
gaccaagtat ccaatctggt tgactgcctg tctgatgagt tctgcctgga cgagaaacgg   1980
gagctgtctg agaaggtcaa gcacgctaag cggctgtctg acgaacggaa cctgcttcaa   2040
gacccgaact tccggggtat caatcgacag ccagatcggg gttggcgggg aagcactgac   2100
atcactatac aaggagggaa tgatgtcttc aaggaaaact acgtcacgct gccgggaacg   2160
tttgacgagt gctacccgac gtacctttat cagaaaatcg acgagtctaa gctgaaatct   2220
gacactcgtt accagttgcg tggttacatt gaggatagcc aggatcttga aatctacctt   2280
attcgttaca acgctaagca cgagacggtc aacgttcctg gaacgtcatt cttgtggccg   2340
```

-continued

```
ctttctgtcg agtcgccgat tgggaagtgc ggggagccca accgttgcgc tccacacatt   2400

gagtggaacc ctgaccttga gtgctcgtgc cgtgatgggg agaagtgcgc tcaccatagt   2460

caccactttt cacttgacat tgatgtcggg tgcacggatc ttaatgagga tcttggggtc   2520

tgggtcatat tcaagattaa gacgcaagat gggcacgcta gactgggaaa cttggagttc   2580

cttgaggaaa agccactgct aggggaagct cttgctagag ctaagcgggc ggagaagaag   2640

tggcgtgata agcgtgagac acttcaactt gagacgaata tcgtttacaa ggaggcgaag   2700

gagtcagtcg atgcgctctt cgtgaatagt caatacgacc gacttcaagc ggataccgat   2760

attgcgatga ttcacgcggc tgataagcgt gtccatcgta ttcgtgaagc gtaccttccg   2820

gagttgtcgg tcattcctgg ggttaatgcg gggatattcg aggaattgga ggggaggata   2880

ttcacggcgt attcgcttta cgatgcgaga aatgttatta agaatgggga tttcaataac   2940

gggttgtcgt gctggaatgt gaaagggcat gttgacattg aggagcaaaa caaccatcgt   3000

agtgttcttg tcgtacctga gtgggaggcc gaggtttcgc aagaggtgcg ggtttgccca   3060

gggcgaggct acatcttgag agttacggcg tacaaagagg gatacgggga gggatgtgtt   3120

acgattcatg agatagagga tcatactgat gagcttaagt tctcaaactg tgttgaggaa   3180

gatgcttacc caggaaatac cgttgcctgt gataactatc ctgcaaacca ggaggaagga   3240

tgcaccgagt tgcgacattc gggaaatcga ggatatgatg agacttatgt taattcaaca   3300

tcatcatcaa ctgattacac tgctgtgtac aaggaggaat catatacggg agaacaacgt   3360

tatgattcat gcgagtcgaa tcgaggatat ggaaactata caccactacc cgctggatat   3420

gtgacaaagg aactagagta tttcccagaa actgataagg tgtggataga gattggtgaa   3480

accgaaggaa cattcatcgt tgactctgtg gaactcttgc ttatggagga atga         3534
```

<210> SEQ ID NO 8
<211> LENGTH: 1812
<212> TYPE: DNA
<213> ORGANISM: Artificial
<220> FEATURE:
<223> OTHER INFORMATION: Synthetic coding sequence used for expression in a plant cell, TIC4029_1PL encoding TIC4029_1.

<400> SEQUENCE: 8

```
atgaacaaca acattgagaa ccagtgcgtg ccctacaact gcctgagcaa ccctgaggag     60

gtgctcctag acggtgagcg catctccacc ggtaactcta gcatcgacat ctccctgagc    120

ctagtgcagc tcctagtgtc taacttcgtg cccggcggtg gcttcctcgt gggcctcatc    180

gacttcgtgt ggggcatcgt gggcccctcc cagtgggacg ccttcctcgt gcagatcgag    240

cagctcatcc agcaacgcat cgaggcctac gcccgcgccg ctgccatcag caacctcgag    300

ggcatcggca acaatttcaa catctacgtg gaggccttcc aggagtggga ggaagacccc    360

aacaatcccg ccacccgcaa ccgcgtggtc gaccgcttcc gcatcctcga cggcctcctg    420

gagcgcgaca tcccctcctt ccgcatctcc ggcttcgagg tgcccctcct gtccgtgtac    480

acccaggccg ctaacctcca cctcgccatc ctccgcgact ccgtgatctt cggcgagcgc    540

tggggcctca ccactaccaa cgtgaacgag aactacaacc gccagatccg ccacatcaac    600

gagtacgccg accactgcgc caacacctac aaccgcggcc tcaacaatct ccccaagtcc    660

acctaccagg actggatcac ctacaaccgc ctccgcaggg acctcaccct caccgtgctc    720

gacatcgtga acttctttcc caactacgac aaccgcaggt accccatcca gaccgtgggc    780

cagctcaccc gcgaggtgta caccgacccc ctcatcaact tcaaccccca gctccagtcc    840
```

-continued

```
gtggcccagc tccccacctt caacgtgatg gagtccagcg ccatccgcaa cccccacctc    900

ttcgacgtgc tcaacaatct caccatcttc accgactggt tctccgtggg ccgcaacttc    960

tactggggcg gtcaccgcgt gatctccagc cgcatcggcg gtggcaacat cacctccccc   1020

atctacggcc gcgaggccaa ccaggagcct ccgcgctcct tcaccttcaa cggccctgtg   1080

ttccgcaccc tctccaaccc taccctcagg tccctccagc aaccttggcc tgcccctccg   1140

ttcaacctca ggggcgtgga gggcgtggag ttctccaccc ctaccaactc cttcacctac   1200

aggggcaggg gcaccgtgga ctccctcacc gagctgcctc cgcaggacaa ctccgtgcct   1260

ccgagggagg gctacagcca caggctgtgc cacgccacct tcgtgcagag gagcggcacc   1320

cctttcctga ccactggcgt cgttttcagc tggacccaca ggagcgccga ccagaacatc   1380

atttacccta acaggatcac ccagatccct ctggtcaagg ccagcgacct gcctagcggc   1440

accactgtcg ttaggggccc tggcttcacc ggcggtgaca tcctgaggcg gaccagcacc   1500

ggcggtttcg gcaccatcag ggtcaacgtc aacggcaccc tgactcagag gtacaggatc   1560

ggcttcaggt acgccagcac tgtcgacttc gacttctttg tcgttagggg cggtactact   1620

gtcaacaatt tcaggttccc gaggactatg aacagcggcg aggaactgag gtacggtagc   1680

ttcgagacta ggtctttcac tacgccgttc actttcactc agatccagga cactatccgg   1740

actagtatcc agggtctgtc tggtaacggt gaggtctacc tggaccggat cgagatcatt   1800

ccggtcactt ga                                                       1812
```

```
<210> SEQ ID NO 9
<211> LENGTH: 1746
<212> TYPE: DNA
<213> ORGANISM: Artificial
<220> FEATURE:
<223> OTHER INFORMATION: Synthetic coding sequence used for expression
      in a plant cell, TIC4029_8PL encoding a TIC4029_8 which comprises
      a truncation at the amino terminus and a truncation of the
      protoxin domain.

<400> SEQUENCE: 9

atgatctcca ccggtaactc tagcatcgac atctccctga gcctagtgca gctcctagtg     60

tctaacttcg tgcccggcgg tggcttcctc gtgggcctca tcgacttcgt gtggggcatc    120

gtgggcccct cccagtggga cgccttcctc gtgcagatcg agcagctcat ccagcaacgc    180

atcgaggcct acgcccgcgc cgctgccatc agcaacctcg agggcatcgg caacaatttc    240

aacatctacg tggaggcctt ccaggagtgg gaggaagacc ccaacaatcc cgccacccgc    300

aaccgcgtgg tcgaccgctt ccgcatcctc gacggcctcc tggagcgcga catcccctcc    360

ttccgcatct ccggcttcga ggtgcccctc ctgtccgtgt acacccaggc cgctaacctc    420

cacctcgcca tcctccgcga ctccgtgatc ttcggcgagc gctggggcct caccactacc    480

aacgtgaacg agaactacaa ccgccagatc cgccacatca acgagtacgc cgaccactgc    540

gccaacacct acaaccgcgg cctcaacaat ctccccaagt ccacctacca ggactggatc    600

acctacaacc gcctccgcag ggacctcacc ctcaccgtgc tcgacatcgt gaacttcttt    660

cccaactacg acaaccgcag gtaccccatc cagaccgtgg gccagctcac ccgcgaggtg    720

tacaccgacc ccctcatcaa cttcaacccc cagctccagt ccgtggccca gctccccacc    780

ttcaacgtga tggagtccag cgccatccgc aacccccacc tcttcgacgt gctcaacaat    840

ctcaccatct tcaccgactg gttctccgtg ggccgcaact tctactgggg cggtcaccgc    900

gtgatctcca gccgcatcgg cggtggcaac atcacctccc ccatctacgg ccgcgaggcc    960
```

-continued

```
aaccaggagc ctccgcgctc cttcaccttc aacggccctg tgttccgcac cctctccaac   1020

cctaccctca ggtccctcca gcaaccttgg cctgcccctc cgttcaacct caggggcgtg   1080

gagggcgtgg agttctccac ccctaccaac tccttcacct acaggggcag gggcaccgtg   1140

gactccctca ccgagctgcc tccgcaggac aactccgtgc ctccgaggga gggctacagc   1200

cacaggctgt gccacgccac cttcgtgcag aggagcggca ccccctttcct gaccactggc   1260

gtcgttttca gctggaccca caggagcgcc gaccagaaca tcatttaccc taacaggatc   1320

acccagatcc ctctggtcaa ggccagcgac ctgcctagcg gcaccactgt cgttaggggc   1380

cctggcttca ccggcggtga catcctgagg cggaccagca ccggcggttt cggcaccatc   1440

agggtcaacg tcaacggcac cctgactcag aggtacagga tcggcttcag gtacgccagc   1500

actgtcgact tcgacttctt tgtcgttagg ggcggtacta ctgtcaacaa tttcaggttc   1560

ccgaggacta tgaacagcgg cgaggaactg aggtacggta gcttcgagac taggtctttc   1620

actacgccgt tcactttcac tcagatccag gacactatcc ggactagtat ccagggtctg   1680

tctggtaacg gtgaggtcta cctggaccgg atcgagatca ttccggtcac tgctactctg   1740

aagtga                                                              1746
```

<210> SEQ ID NO 10
<211> LENGTH: 581
<212> TYPE: PRT
<213> ORGANISM: Artificial
<220> FEATURE:
<223> OTHER INFORMATION: Amino acid sequence of the TIC4029_8 pesticidal protein comprising a truncation at the amino terminus and a truncation of the protoxin domain.

<400> SEQUENCE: 10

```
Met Ile Ser Thr Gly Asn Ser Ser Ile Asp Ile Ser Leu Ser Leu Val
1               5                   10                  15

Gln Leu Leu Val Ser Asn Phe Val Pro Gly Gly Gly Phe Leu Val Gly
            20                  25                  30

Leu Ile Asp Phe Val Trp Gly Ile Val Gly Pro Ser Gln Trp Asp Ala
        35                  40                  45

Phe Leu Val Gln Ile Glu Gln Leu Ile Gln Gln Arg Ile Glu Ala Tyr
    50                  55                  60

Ala Arg Ala Ala Ala Ile Ser Asn Leu Glu Gly Ile Gly Asn Asn Phe
65                  70                  75                  80

Asn Ile Tyr Val Glu Ala Phe Gln Glu Trp Glu Glu Asp Pro Asn Asn
                85                  90                  95

Pro Ala Thr Arg Asn Arg Val Val Asp Arg Phe Arg Ile Leu Asp Gly
            100                 105                 110

Leu Leu Glu Arg Asp Ile Pro Ser Phe Arg Ile Ser Gly Phe Glu Val
        115                 120                 125

Pro Leu Leu Ser Val Tyr Thr Gln Ala Ala Asn Leu His Leu Ala Ile
    130                 135                 140

Leu Arg Asp Ser Val Ile Phe Gly Glu Arg Trp Gly Leu Thr Thr Thr
145                 150                 155                 160

Asn Val Asn Glu Asn Tyr Asn Arg Gln Ile Arg His Ile Asn Glu Tyr
                165                 170                 175

Ala Asp His Cys Ala Asn Thr Tyr Asn Arg Gly Leu Asn Asn Leu Pro
            180                 185                 190

Lys Ser Thr Tyr Gln Asp Trp Ile Thr Tyr Asn Arg Leu Arg Arg Asp
        195                 200                 205
```

-continued

```
Leu Thr Leu Thr Val Leu Asp Ile Val Asn Phe Phe Pro Asn Tyr Asp
    210                 215                 220

Asn Arg Arg Tyr Pro Ile Gln Thr Val Gly Gln Leu Thr Arg Glu Val
225                 230                 235                 240

Tyr Thr Asp Pro Leu Ile Asn Phe Asn Pro Gln Leu Gln Ser Val Ala
                245                 250                 255

Gln Leu Pro Thr Phe Asn Val Met Glu Ser Ser Ala Ile Arg Asn Pro
            260                 265                 270

His Leu Phe Asp Val Leu Asn Asn Leu Thr Ile Phe Thr Asp Trp Phe
        275                 280                 285

Ser Val Gly Arg Asn Phe Tyr Trp Gly Gly His Arg Val Ile Ser Ser
    290                 295                 300

Arg Ile Gly Gly Gly Asn Ile Thr Ser Pro Ile Tyr Gly Arg Glu Ala
305                 310                 315                 320

Asn Gln Glu Pro Pro Arg Ser Phe Thr Phe Asn Gly Pro Val Phe Arg
                325                 330                 335

Thr Leu Ser Asn Pro Thr Leu Arg Ser Leu Gln Gln Pro Trp Pro Ala
            340                 345                 350

Pro Pro Phe Asn Leu Arg Gly Val Glu Gly Val Glu Phe Ser Thr Pro
        355                 360                 365

Thr Asn Ser Phe Thr Tyr Arg Gly Arg Gly Thr Val Asp Ser Leu Thr
    370                 375                 380

Glu Leu Pro Pro Gln Asp Asn Ser Val Pro Pro Arg Glu Gly Tyr Ser
385                 390                 395                 400

His Arg Leu Cys His Ala Thr Phe Val Gln Arg Ser Gly Thr Pro Phe
                405                 410                 415

Leu Thr Thr Gly Val Val Phe Ser Trp Thr His Arg Ser Ala Asp Gln
            420                 425                 430

Asn Ile Ile Tyr Pro Asn Arg Ile Thr Gln Ile Pro Leu Val Lys Ala
        435                 440                 445

Ser Asp Leu Pro Ser Gly Thr Thr Val Val Arg Gly Pro Gly Phe Thr
    450                 455                 460

Gly Gly Asp Ile Leu Arg Arg Thr Ser Thr Gly Gly Phe Gly Thr Ile
465                 470                 475                 480

Arg Val Asn Val Asn Gly Thr Leu Thr Gln Arg Tyr Arg Ile Gly Phe
                485                 490                 495

Arg Tyr Ala Ser Thr Val Asp Phe Asp Phe Phe Val Val Arg Gly Gly
            500                 505                 510

Thr Thr Val Asn Asn Phe Arg Phe Pro Arg Thr Met Asn Ser Gly Glu
        515                 520                 525

Glu Leu Arg Tyr Gly Ser Phe Glu Thr Arg Ser Phe Thr Thr Pro Phe
    530                 535                 540

Thr Phe Thr Gln Ile Gln Asp Thr Ile Arg Thr Ser Ile Gln Gly Leu
545                 550                 555                 560

Ser Gly Asn Gly Glu Val Tyr Leu Asp Arg Ile Glu Ile Ile Pro Val
                565                 570                 575

Thr Ala Thr Leu Lys
            580
```